US009662322B2

(12) United States Patent
Knappertz

(10) Patent No.: US 9,662,322 B2
(45) Date of Patent: May 30, 2017

(54) LAQUINIMOD FOR THE TREATMENT OF RELAPSING-REMITTING MULTIPLE SCLEROSIS (RRMS) PATIENTS WITH A HIGH DISABILITY STATUS

(71) Applicant: Volker Knappertz, Potomac, MD (US)

(72) Inventor: Volker Knappertz, Potomac, MD (US)

(73) Assignee: TEVA PHARMACEUTICAL INDUSTRIES, LTD., Petach-Tikva (IL)

( * ) Notice: Subject to any disclaimer, the term of this patent is extended or adjusted under 35 U.S.C. 154(b) by 0 days.

(21) Appl. No.: 14/946,586

(22) Filed: Nov. 19, 2015

(65) Prior Publication Data

US 2016/0074378 A1 Mar. 17, 2016

Related U.S. Application Data

(63) Continuation of application No. 14/698,319, filed on Apr. 28, 2015.

(60) Provisional application No. 61/985,886, filed on Apr. 29, 2014, provisional application No. 62/046,561, filed on Sep. 5, 2014, provisional application No. 62/119,506, filed on Feb. 23, 2015, provisional application No. 62/139,978, filed on Mar. 30, 2015.

(51) Int. Cl.
| | |
|---|---|
| *A61K 31/4704* | (2006.01) |
| *A61P 37/02* | (2006.01) |
| *A61K 31/47* | (2006.01) |
| *A61J 1/00* | (2006.01) |
| *A61B 5/00* | (2006.01) |
| *A61B 5/11* | (2006.01) |
| *A61K 38/21* | (2006.01) |
| *A61K 45/06* | (2006.01) |

(52) U.S. Cl.
CPC .............. *A61K 31/47* (2013.01); *A61B 5/112* (2013.01); *A61B 5/4082* (2013.01); *A61J 1/00* (2013.01); *A61K 31/4704* (2013.01); *A61K 38/215* (2013.01); *A61K 45/06* (2013.01)

(58) Field of Classification Search
CPC A61K 31/4704; C07D 215/56; A61B 5/4082; A61B 5/112
USPC ................... 514/312; 546/153, 155; 544/128
See application file for complete search history.

(56) References Cited

U.S. PATENT DOCUMENTS

| | | | |
|---|---|---|---|
| 4,107,310 A | 8/1978 | Allais et al. | |
| 4,547,511 A | 10/1985 | Eriksoo et al. | |
| 4,738,971 A | 4/1988 | Eriksoo et al. | |
| 5,716,638 A | 2/1998 | Touitou | |
| 5,912,349 A | 6/1999 | Sih | |
| 6,077,851 A | 6/2000 | Bjork et al. | |
| 6,121,287 A | 9/2000 | Bjork et al. | |
| 6,133,285 A | 10/2000 | Bjork et al. | |
| 6,395,750 B1 | 5/2002 | Hedlund et al. | |
| 6,593,343 B2 | 7/2003 | Bjork et al. | |
| 6,605,616 B1 | 8/2003 | Bjork et al. | |
| 6,875,869 B2 | 4/2005 | Jansson | |
| 7,560,557 B2 | 7/2009 | Jansson | |
| 7,589,208 B2 | 9/2009 | Jansson et al. | |
| 7,884,208 B2 | 2/2011 | Frankel et al. | |
| 7,989,473 B2 | 8/2011 | Patashnik et al. | |
| 8,178,127 B2 | 5/2012 | Safadi et al. | |
| 8,252,933 B2 | 8/2012 | Grant et al. | |
| 8,314,124 B2 | 11/2012 | Jansson et al. | |
| 8,338,453 B2 | 12/2012 | Kalafer et al. | |
| 8,383,645 B2 | 2/2013 | Patashnik et al. | |
| 2002/0173520 A1 | 11/2002 | Bjork et al. | |
| 2005/0192315 A1 | 9/2005 | Jansson et al. | |
| 2005/0215586 A1 | 9/2005 | Jansson et al. | |
| 2006/0276393 A1 | 12/2006 | Milburn et al. | |
| 2009/0048181 A1 | 2/2009 | Schipper et al. | |
| 2009/0081259 A1 | 3/2009 | Jonas et al. | |
| 2009/0148462 A1 | 6/2009 | Chevrier et al. | |
| 2009/0258847 A1 | 10/2009 | Schreiner et al. | |
| 2010/0322900 A1 | 12/2010 | Tarcic et al. | |
| 2011/0027219 A1 | 2/2011 | Tarcic et al. | |
| 2011/0034508 A1 | 2/2011 | Hayardeny | |
| 2011/0112141 A1 | 5/2011 | Frenkel et al. | |

(Continued)

FOREIGN PATENT DOCUMENTS

| | | |
|---|---|---|
| EP | 1073639 | 2/2001 |
| EP | 1095021 | 5/2001 |

(Continued)

OTHER PUBLICATIONS

Ford Neurology 2012, 78(1), Meeting Abstracts P05.091.*
Goldman et al. Ther. Adv. Neurol. Disord. 2010, 3(4), 229-239.*
Comi et al. N. Engl. J. Med. 2012, 366 (11), 1000-1009.*
PCT International Preliminary Report on Patentability issued Dec. 20, 2011 in connection with PCT International Application No. PCT/US2010/001759.
PCT International Search Report issued Aug. 19, 2010 in connection with PCT International Application No. PCT/US2010/001759.
Written Option of the International Searching Authority issued Aug. 19, 2010 in connection with PCT International Application No. PCT/US2010/001759.
PCT International Preliminary Report on Patentability issued Jun. 12, 2013 in connection with PCT International Application No. PCT/US2011/063460.
PCT International Search Report issued Apr. 3, 2012 in connection with PCT International Application No. PCT/US2011/063460.

(Continued)

*Primary Examiner* — Irina Neagu
(74) *Attorney, Agent, or Firm* — John P. White; Gary J. Gershik; Cooper & Dunham LLP

(57) ABSTRACT

This invention provides a method for treating or for reducing ambulatory deterioration in a human patient diagnosed to be afflicted with relapsing-remitting multiple sclerosis (RRMS) and having a high baseline disability score according to the Kurtzke Expanded Disability Status Scale (EDSS), comprising periodically administering to only the patient diagnosed with RRMS and having a high baseline disability score an amount of laquinimod effective to treat the patient or to reduce ambulatory deterioration. This invention further provides pharmaceutical compositions and packages comprising an effective amount of laquinimod for treating a human patient diagnosed to be afflicted with RRMS and having a high baseline disability score according to the EDSS.

28 Claims, 2 Drawing Sheets

(56) References Cited

U.S. PATENT DOCUMENTS

| | | |
|---|---|---|
| 2011/0118308 A1 | 5/2011 | Frenkel et al. |
| 2011/0217295 A1 | 9/2011 | Haviv et al. |
| 2011/0218179 A1 | 9/2011 | Haviv et al. |
| 2011/0218203 A1 | 9/2011 | Kaye et al. |
| 2011/0251235 A1 | 10/2011 | Patachnik et al. |
| 2012/0010238 A1 | 1/2012 | Piryatinsky |
| 2012/0010239 A1 | 1/2012 | Fristedt |
| 2012/0142730 A1 | 6/2012 | Tarcic et al. |
| 2012/0225070 A1 | 9/2012 | Smith et al. |
| 2012/0225124 A1 | 9/2012 | Safadi et al. |
| 2012/0252758 A1 | 10/2012 | Pettersson et al. |
| 2012/0302600 A1 | 11/2012 | Patashnik et al. |
| 2013/0028866 A1 | 1/2013 | Gilgun |
| 2013/0029916 A1 | 1/2013 | Gilgun |
| 2013/0096158 A1 | 4/2013 | Hallak et al. |
| 2013/0184310 A1 | 7/2013 | Haviv et al. |
| 2013/0203807 A1 | 8/2013 | Tarcic et al. |
| 2013/0217724 A1 | 8/2013 | Ioffe et al. |
| 2013/0259856 A1 | 10/2013 | Kaye |
| 2013/0272996 A1 | 10/2013 | Tarcic et al. |
| 2013/0303569 A1 | 11/2013 | Bar-Zohar |
| 2013/0324574 A1 | 12/2013 | Laxer |
| 2013/0345256 A1 | 12/2013 | Laxer |
| 2013/0345257 A1 | 12/2013 | Hahn et al. |
| 2014/0017226 A1 | 1/2014 | Kaye |
| 2014/0018386 A1 | 1/2014 | Sarfati et al. |
| 2014/0024678 A1 | 1/2014 | Safadi et al. |
| 2014/0045886 A1 | 2/2014 | Martino |
| 2014/0045887 A1 | 2/2014 | Martino |
| 2014/0051723 A1 | 2/2014 | Piryatinsky et al. |
| 2014/0057883 A1 | 2/2014 | Tarcic et al. |
| 2014/0105850 A1 | 4/2014 | Tarcic |
| 2014/0107154 A1 | 4/2014 | Filippi |
| 2014/0128430 A1 | 5/2014 | Frenkel |
| 2014/0171647 A1 | 6/2014 | Frenkel et al. |
| 2014/0235670 A1 | 8/2014 | Tarcic et al. |
| 2014/0271878 A1 | 9/2014 | Frenkel et al. |
| 2015/0037263 A1 | 2/2015 | Hallak et al. |
| 2015/0037318 A1 | 2/2015 | Silver et al. |
| 2015/0056281 A1 | 2/2015 | Gilgun |
| 2015/0094332 A1 | 4/2015 | Knappertz et al. |
| 2015/0119420 A1 | 4/2015 | Kaye |
| 2015/0306088 A1* | 10/2015 | Knappertz ......... A61K 31/4704 514/312 |
| 2016/0074380 A1 | 3/2016 | Hayden et al. |

FOREIGN PATENT DOCUMENTS

| | | | |
|---|---|---|---|
| EP | 1097139 | 5/2001 | |
| EP | 1511732 | 3/2005 | |
| EP | 1720531 | 11/2006 | |
| WO | WO 99/55678 | 11/1999 | |
| WO | WO 00/03991 | 1/2000 | |
| WO | WO 00/03992 | 1/2000 | |
| WO | WO 03/106424 | 12/2003 | |
| WO | WO 2005/074899 | 8/2005 | |
| WO | WO 2007/146248 | 12/2007 | |
| WO | WO 2008/097596 | 8/2008 | |
| WO | WO 2010/001257 | 1/2010 | |
| WO | WO 2010/147665 | 12/2010 | |
| WO | WO 2013/016686 | * 1/2013 | ............. A01N 43/42 |

OTHER PUBLICATIONS

Written Option of the International Searching Authority issued Apr. 3, 2012 in connection with PCT International Application No. PCT/US2011/063460.

Written Option of the International Searching Authority issued Dec. 9, 2013 in connection with PCT International Application No. PCT/US2013/64061.

PCT International Search Report issued Dec. 9, 2013 in connection with PCT International Application No. PCT/US2013/64061.

PCT International Search Report issued May 19, 2014 in connection with PCT International Application No. PCT/US2014/16278.

Written Option of the International Searching Authority issued May 19, 2015 in connection with PCT International Application No. PCT/US2014/16278.

Dec. 27, 2011 Office Action issued by the U.S. Patent and Trademark Office in connection U.S. Appl. No. 12/803,121.

May 29, 2012 Amendment in Response to Dec. 27, 2011 Office action filed with the U.S. Patent and Trademark Office in connection with U.S. Appl. No. 12/803,121.

Jul. 12, 2012 Final Office Action issued by the U.S. Patent and Trademark Office in connection with U.S. Appl. No. 12/803,121.

Aug. 20, 2013 Office Action issued by the U.S. Patent and Trademark Office in connection with U.S. Appl. No. 13/712,398.

Apr. 14, 2014 Office Action issued by the U.S. Patent and Trademark Office in connection with U.S. Appl. No. 14/137,778.

Aug. 14, 2014 Response to Apr. 14, 2014 Office Action filed with the U.S. Patent and Trademark Office in connection with U.S. Appl. No. 14/137,778.

Oct. 28, 2015 Final Office Action issued by the U.S. Patent and Trademark Office in connection with U.S. Appl. No. 14/137,778.

Sep. 4, 2015 Office Action issued by the U.S. Patent and Trademark Office in connection with U.S. Appl. No. 14/635,837.

Oct. 16, 2014 Office Action issued by the U.S. Patent and Trademark Office in connection with U.S. Appl. No. 14/049,411.

Jan. 16, 2015 Response to Oct. 16, 2014 Office Action filed U.S. Patent and Trademark Office in connection with U.S. Appl. No. 14/049,411.

Mar. 30, 2015 Final Office Action issued by the U.S. Patent and Trademark Office in connection with U.S. Appl. No. 14/049,411.

Jun. 22, 2015 Advisory Action issued by the U.S. Patent and Trademark Office in connection with U.S. Appl. No. 14/049,411.

Aug. 28, 2015 Response to Mar. 30, 2015 Final Office Action and Jun. 22, 2015 Advisory Action filed with the U.S. Patent and Trademark Office in connection with U.S. Appl. No. 14/049,411.

Oct. 23, 2015 Office Action issued by the U.S. Patent and Trademark Office in connection with U.S. Appl. No. 14/180,173.

Feb. 24, 2014 Office Action issued by the U.S. Patent and Trademark Office in connection with U.S. Appl. No. 13/312,284.

May 27, 2014 Response to Feb. 24, 2014 Office Action filed with the U.S. Patent and Trademark Office in connection with U.S. Appl. No. 13/312,284.

Oct. 7, 2015 Office Action issued by the U.S. Patent and Trademark Office in connection with U.S. Appl. No. 13/312,284.

Dec. 30, 2015 Office Action issued by the U.S. Patent and Trademark Office in connection with U.S. Appl. No. 14/698,319.

Oct. 2, 2012 Extended European Search Report issued by the European patent Office (EPO) in connection with European Patent Application No. 10 78 9873.

Sep. 20, 2012 Supplementary European Search Report issued in connection with European Patent Application No. 10 78 9873.

Apr. 16, 2013 Response to Oct. 2, 2012 Extended European Search Report issued in connection with European Patent Application No. 10 78 9873.

Apr. 16, 2013 Response to Sep. 20, 2012 Supplementary European Search Report issued in connection with European Patent Application No. 10 78 9873.

Jan. 2, 2014 European Office Action issued by the European patent Office (EPO) in connection with European Patent Application No. 10789873.6.

May 7, 2013 Response to Mar. 5, 2013 Mexican Office Action in connection with Mexican Patent Application No. MX/a/2011/013902.

Mar. 5, 2013 Mexican Office Action issued in connection with Mexican Patent Application No. MX/a/2011/013902.

Mar. 4, 2014 Mexican Office Action issued in connection with Mexican Patent Application No. MX/a/2011/013902.

Nov. 14, 2014 Fourth Office Action issued in connection with Mexican Patent Application No. MX/a/2011/013902, including English language translation.

Mar. 27, 2015 Response to Nov. 14, 2014 filed in connection with Mexican Patent Application No. MX/a/2011/013902.

Oct. 3, 2012 Examiners Report issued by the New Zealand Patent Office in connection with New Zealand Patent Application No. 597378.

(56) References Cited

OTHER PUBLICATIONS

Jan. 23, 2014 New Zealand Office Action issued by the New Zealand Patent Office in connection with New Zealand Application No. 597378.
Oct. 28, 2013 Eurasian Office Action issued in connection with Eurasian Patent Application No. 201270041.
Feb. 14, 2014 Response to Oct. 28, 2013 European Office Action issued by the European patent Office (EPO) in connection with Eurasian Patent Application No. 201270041.
Oct. 14, 2015 Office Action issued by the Chilean Patent Office in connection with Chilean Patent Application No. 2013-1602.
May 30, 2014 First Office Action issued by the Chinese Patent Office in connection with Chines Patent Application No. 201180060414.8.
Oct. 14, 2014 Response to May 30, 2014 First Office Action filed with the Chinese Patent Office in connection with Chines Patent Application No. 201180060414.8.
Apr. 17, 2015 Official Action issued by the Eurasian Patent Office in connection with Eurasian Patent Application No. 201390827.
Nov. 10, 2015 Amendment in Response to Apr. 17, 2015 Official Action filed with the Eurasian Patent Office in connection with Eurasian Patent Application No. 201390827.
May 13, 2015 Eurasian Search Report issued by the Eurasian Patent Office in connection with Eurasian Patent Application No. 201390827.
Mar. 27, 2014 Supplementary European Search Report issued by the European Patent Office in connection with European Patent Application No. 11846599.6.
May 30, 2014 Communication pursuant to Article 94(3) EPC issued by the European Patent Office in connection with European Patent Application No. 11846599.6.
Sep. 30, 2014 Response to May 30, 2014 Communication pursuant to Article 94(3) EPC filed with the European Patent Office in connection with European Patent Application No. 11846599.6.
Nov. 18, 2015 Communication pursuant to Article 94(3) EPC issued by the European Patent Office in connection with European Patent Application No. 11846599.6.
May 7, 2015 First Office Action issued by the Mexican Patent Office in connection with Mexican Patent Application No. MX/a/2013/006464.
Nov. 11, 2013 Examination Report issued by the New Zealand Patent Office in connection with New Zealand Patent Application No. 611628.
Feb. 3, 2015 Response to Nov. 11, 2013 Examination Report filed with the New Zealand Patent Office in connection with New Zealand Patent Application No. 611628.
Feb. 20, 2015 Further Examination Report issued by the New Zealand Patent Office in connection with New Zealand Patent Application No. 611628.
May 20, 2015 Response to Feb. 20, 2015 Further Examination Report filed with the New Zealand Patent Office in connection with New Zealand Patent Application No. 611628.
Sep. 30, 2014 Office Action issued by the Vietnamese Patent Office in connection with Vietnamese Patent Application No. 1-2014-02078, including English language translation.
Dec. 1, 2014 Response to Sep. 30, 2014 Office Action filed with the Vietnamese Patent Office in connection with Vietnamese Patent Application No. 1-2014-02078, including English language translation.
Jun. 22, 2015 Notice of Final Refusal issued by the Bolivian Patent Office in connection with Bolivian Patent Application No. SP-00138-2013, including English language translation.
Jul. 9, 2015 Response to Jun. 22, 2015 Notice of Final Refusal filed with the Bolivian Patent Office in connection with Bolivian Patent Application No. SP-00138-2013.
Opposition filed by Chilean Pharmaceutical Labs Industrial Association in connection with Chilean Patent Application No. 2935-2014.
Opposition filed by Labortorios Recalcine S. A. in connection with Chilean Patent Application No. 2935-2014.

Oct. 10, 2015 Office Action issued by the Chinese Patent Office in connection with Chinese Patent Application No. 201380022530.x, including English language translation.
Jul. 31, 2015 First Examination Report issued by the New Zealand Patent Office in connection with New Zealand Patent Application No. 630557.
Oct. 8, 2015 First Examination Report issued by the New Zealand Patent Office in connection with New Zealand Patent Application No. 630725.
Sep. 30, 2015 Notice issued by the Vietnamese Patent Office in connection with Vietnamese Patent Application No. 1-2015-03272.
Oct. 28, 2015 Response to Sep. 30, 2015 Notice issued by the Vietnamese Patent Office in connection with Vietnamese Patent Application No. 1-2015-03272.
Oct. 27, 2015 Official Action issued by the Bolivian Patent Office in connection with Bolivian Patent Application No. SP 00041-2014.
Alroudhani et al. (2013) "Use of natalizumab in patients with active relapsing-remitting multiple sclerosis in Kuwait", Med Princ Pract. 22(5):495-9 (abstract only).
Barkhof F. (1999) "MRI in Multiple Sclerosis: Correlation with Expanded Disability Status Scale (EDSS)", Multiple Sclerosis. 5 (4) :283-286.
Boneschi et al. (2003) Effects of glatiramer acetate on relapse rate and accumulated disability in multiple sclerosis; meta-analysis of three double-blind, randomized, placebo-controlled clinical trials. Multi Scler. 9(4):349-355.
Cobo-Calvo et al. (2015) "Effectiveness of Natalizumab in Patients with Highly Active Relapsing Remitting Multiple Sclerosis", Eur Neurol. 73:220-229.
Comi et al. (2007) LAQ/5062 Study Group. "The Effect of Two Doses of Laquinimod on MRI-Monitored Disease Activity in Patients with Relapsing-Remitting Multiple Sclerosis: A Multi-Center, Randomized, Double-Blind, Placebo-Controlled Study", Presented at: 59th Annual Meeting of the American Academy of Neurology; Apr. 28-May 5, 2007, Boston, MA.
Comi et al. (2008) "Effect of laquinimod on MRI-monitored disease activity in patients with relapsing-remitting multiple sclerosis: a multicentre, randomized, double-blind, placebocontrolled phase Iib study" Lancet. Jun. 21, 2008; 371 (9630) :2085-92.
De Stefano et al. (1999) "Evidence of early axonal damage in patients with multiple sclerosis", Arch Neural. 2001; 58: 65-70.
Dutta and Trapp (2011) "Mechanisms of Neuronal Dysfunction and Degeneration in Multiple Sclerosis", Prog Neurobiol. Jan. 2011 ; 93(1): 1-12.
EMEA Guideline on Clinical Investigation of Medicinal Products for the Treatment of Multiple Sclerosis (CPMP/EWP/561/98 Rev. 1, Nove.2006).
Hohlfeld et al. (2000) "The neuroprotective effect of inflammation: implications for the therapy of multiple sclerosis", J Neuroimmunol. 107(2000):161-166.
Kallweit et al. (2012) "Sustained efficacy of natalizumab in the treatment of relapsing-remitting multiple sclerosis independent of disease activity and disability at baseline: real-life data from a Swiss cohort", Clin Neuropharmacol. 35(2) :77-80 (abstract only).
Karussis et al. (1996) "Treatment of secondary progressive multiple sclerosis with the immunomodulator linomide: a doubleblind, placebo-controlled pilot study with monthly magnetic resonance imaging evaluation" Neurology. Aug.;47(2):341-6.
Lehmann et al. (1997) "Inhibition of the progression of multiple sclerosis by linomide is associated with upregulation of CD4+/CD45RA+ cells and downregulation of CD4+/CD45RO+ cells" Clin Immunol Immunopathol. Nov. 1997;85(2):202-9.
Lublin et al. (2014) "Defining the clinical course of multiple sclerosis: The 2013 revisions", Neurology, May 28, 2014, retrieved from the Internet: URL: http://www.neurology.org/content/early/2014/05/28/WNL.0000000000000560.full.html.
Miki, Y, et al. (1999) "Relapsing-Remitting Multiple Sclerosis: Longitudinal Analysis of MR Images—Lack of Correlation between Changes in T2 Lesion Volume and Clinical Findings", Radiology. 213:395-399.
Neuhaus et al. (2003) "Immunomodulation in multiple sclerosis: from immunosuppression to neuroprotechtion", Trends Pharmacol Sci. 24:131-138.

(56) References Cited

OTHER PUBLICATIONS

Noseworthy JH, Lucchinetti C, Rodriguez M, Weinshenker BO. (2000) "Multiple sclerosis", N. Engl J Med. 343:938-952.

Polman et al., (2005) "Diagnostic criteria for multiple sclerosis: 2005 revisions to the McDonald Criteria", Annals of Neurology 58 (6):840-6.

Polman et al., (2005) "Treatment with laquinimod reduces development of active MRI lesions in relapsing MS", Neurology 64:987-991.

Prosperini et al. (2012) "Predictors of freedom from disease activity in natalizumab treated-patients with multiple sclerosis", Journal of the Neurological Sciences. 323:104-112.

Reagan-Shaw et al. (2007) "Dose translation from animal to human studies revisited" FASEB J 22:659-661.

Rudick R. (1999) "Disease-Modifying Drugs for Relapsing-Remitting Multiple Sclerosis and Future Directions for Multiple Sclerosis Therapeutics", Neurotherpatueics 56:1079-1084.

Sargento-Freitas et al. (2013) "Clinical predictors of anoptimal response tonatalizumab inmultiple sclerosis", Journal of Clinical Neuroscience. 20:659-662.

Sandberg-Wollheim et al. (2005) "48-Week Open Safety Study with a High-Dose Oral Laquinimod in MS Patients" Therapy-Immunomodulation—Part II, Sep. 30, 2005, 15:30-17:00 (Abstract only).

Teva Press Release, Laquinimod Demonstrated Significant and sustained Impact on Multiple Sclerosis Disease Activity, Sep. 18, 2008.

U.S. Department of Health and Human Services, Food and Drug Administration, Center for Drug Evaluation and Research, "Guidance for Industry-Estimating the Maximum Safe Starting Dose in Initial Clinical Trials for Therapeutics in Adult Healthy Volunteers" date Jul. 2005.

Wylezinska et al. (2003) "Thatamic neurodegeneration in relapsingremitting multiple sclerosis", Neurology 60:1949-54.

\* cited by examiner

Effect size = 59%

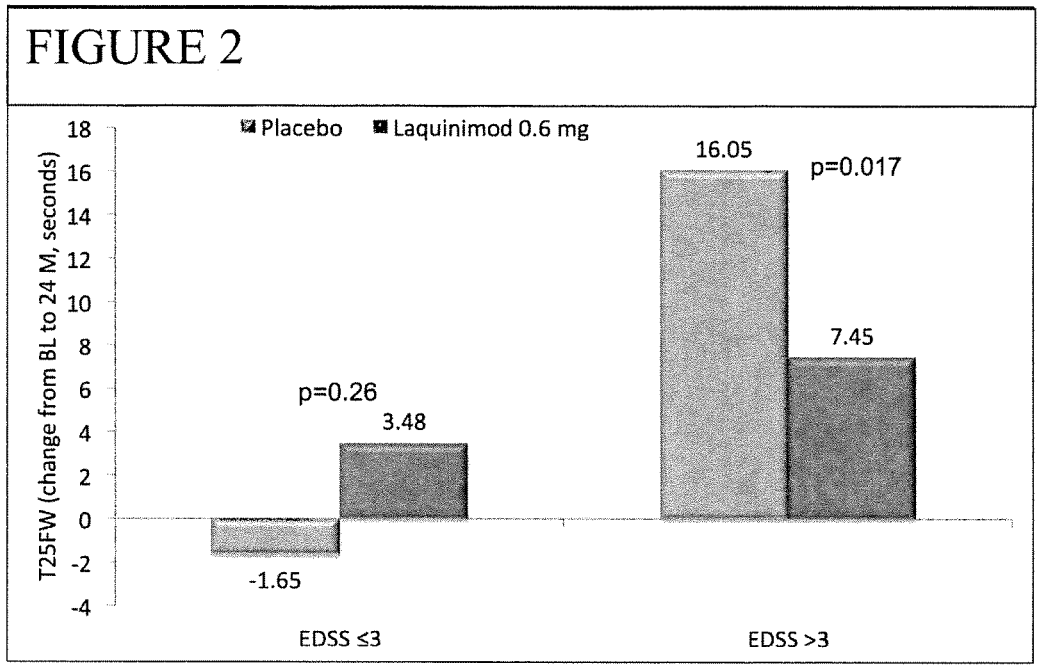

LAQUINIMOD FOR THE TREATMENT OF RELAPSING-REMITTING MULTIPLE SCLEROSIS (RRMS) PATIENTS WITH A HIGH DISABILITY STATUS

This application is a continuation of U.S. Ser. No. 14/698,319, filed Apr. 28, 2015, which claims benefit of U.S. Provisional Application No. 61/985,886, filed Apr. 29, 2014, U.S. Provisional Application No. 62/046,561, filed Sep. 5, 2014, U.S. Provisional Application No. 62/119,506, filed Feb. 23, 2015, and U.S. Provisional Application No. 62/139,978, filed Mar. 30, 2015, the entire content of each of which are hereby incorporated by reference herein.

Throughout this application, various publications are referred to by first author and year of publication. Full citations for these publications are presented in a References section immediately before the claims. Disclosures of the publications cited in the References section in their entireties are hereby incorporated by reference into this application in order to more fully describe the state of the art as of the date of the invention described herein.

BACKGROUND

Multiple Sclerosis (MS) is a neurological disease affecting more than 1 million people worldwide. It is the most common cause of neurological disability in young and middle-aged adults and has a major physical, psychological, social and financial impact on subjects and their families, friends and bodies responsible for health care. (EMEA Guideline, 2006) It is generally assumed that MS is mediated by some kind of autoimmune process possibly triggered by infection and superimposed upon a genetic predisposition. It is a chronic inflammatory condition that damages the myelin of the Central Nervous System (CNS). The pathogenesis of MS is characterized by the infiltration of autoreactive T-cells from the circulation directed against myelin antigens into the CNS. (Bjartmar, 2002) In addition to the inflammatory phase in MS, axonal loss occurs early in the course of the disease and can be extensive over time, leading to the subsequent development of progressive, permanent, neurologic impairment and, frequently, severe disability. (Neuhaus, 2003) Symptoms associated with the disease include fatigue, spasticity, ataxia, weakness, bladder and bowel disturbances, sexual dysfunction, pain, tremor, paroxysmal manifestations, visual impairment, psychological problems and cognitive dysfunction. (EMEA Guideline, 2006)

Various MS disease stages and/or types are described in *Multiple Sclerosis Therapeutics*. (Duntiz, 1999) Among them, relapsing-remitting MS (RRMS) is the most common form at the time of initial diagnosis. Many subjects with RRMS have an initial relapsing-remitting course for 5-15 years, which then advances into the secondary progressive MS (SPMS) disease course. Relapses result from inflammation and demyelination, whereas restoration of nerve conduction and remission is accompanied by resolution of inflammation, redistribution of sodium channels on demyelinated axons and remyelination. (Neuhaus, 2003; Noseworthy, 2000)

In April 2001, an international panel in association with the National MS Society of America recommended diagnostic criteria for MS. These criteria became known as the McDonald Criteria, which make use of MRI techniques and are intended to replace the Poser Criteria and the older Schumacher Criteria. (McDonald, 2001) The McDonald Criteria was revised in March 2005 by an international panel. (Polman, 2005)

Intervention with disease-modifying therapy at relapsing stages of MS is suggested to reduce and/or prevent accumulating neurodegeneration. (Hohlfeld, 2000; De Stefano, 1999) Disease-modifying medications currently approved for use in relapsing MS (RMS; which includes RRMS and SPMS; The Disease Modifying Drug Brochure, 2006) include interferon beta 1-a (Avonex® and Rebif®), interferon beta 1-b (Betaseron®), glatiramer acetate) (Copaxone®), mitoxantrone (Novantrone®) and natalizumab) (Tysabri®). Most of them are believed to act as immunomodulators. Mitoxantrone and natalizumab are believed to act as immunesuppressants. However, the mechanisms of action of each have been only partly elucidated. Immunosuppressants or cytotoxic agents are sometimes used after failure of conventional therapies. However, the relationship between changes of the immune response induced by these agents and the clinical efficacy in MS is far from settled. (EMEA Guideline, 2006) Other therapeutic approaches include symptomatic treatment which refers to all therapies applied to improve the symptoms caused by the disease (EMEA Guideline, 2006) and treatment of acute relapses with corticosteroids. While steroids do not affect the course of MS over time, they can reduce the duration and severity of attacks in some subjects.

Laquinimod sodium is a novel synthetic compound with high oral bioavailability, which has been suggested as an oral formulation for the treatment of MS. (Polman, 2005; Sandberg-Wollheim, 2005) Studies have shown laquinimod to reduce development of active MRI lesions in relapsing MS. (Polman, 2005) However, the clinical significance of MRI brain lesion reduction alone is still unsettled. Although MRI lesions are used as the primary outcome measure in some studies, others have suggested that correlation between MRI abnormalities and clinical disease activity in RRMS patients is weak and that such measurement should be used as secondary outcomes rather than as surrogate markers of clinical responses. (Rudick, 1999; Miki, 1999; Barkhof, 1999) Further, according to pharmaceutical regulatory bodies such as the European Medicines Agency (EMEA), the correlation between MRI results and clinical outcomes has not been proved strong enough so as to accept MRI results as validated surrogate endpoint in pivotal studies. Therefore, according to the EMEA, the relevant efficacy parameter for clinical trials is the accumulation of disability and relapse rate (for RRMS). (EMEA Guideline, 2006) Thus, relapse rate and disability progression are the currently accepted indicators of effectiveness of a RRMS treatment.

The EMEA MS clinical trials guideline further states that the annual relapse rate in RRMS is usually low and that, generally, disability progression takes years. Consequently, confirmatory studies with products intended to modify the course of the disease should be large scale and long enough to have a substantial proportion of patients suffering relapses or showing progression of disability. Two years is considered the minimum duration to demonstrate efficacy. (EMEA Guideline, 2006)

SUMMARY OF THE INVENTION

The subject invention provides a method of treating a human patient diagnosed to be afflicted with relapsing-remitting multiple sclerosis (RRMS) and having a high baseline disability score according to the Kurtzke Expanded Disability Status Scale (EDSS), comprising periodically administering to only the patient diagnosed with RRMS and having a high baseline disability score an amount of laquinimod effective to treat the patient.

The subject invention also provides a method of treating a human patient afflicted with relapsing-remitting multiple sclerosis (RRMS), comprising a) diagnosing the patient as having a high baseline disability score according to the Kurtzke Expanded Disability Status Scale (EDSS), and b) administering to the patient an amount of laquinimod effective to treat the patient only if the patient has been diagnosed as having a high baseline disability score.

The subject invention also provides a method of treating a human patient diagnosed to be afflicted with relapsing-remitting multiple sclerosis (RRMS) and having a baseline disability score according to the Kurtzke Expanded Disability Status Scale (EDSS) of greater than 3.0, comprising periodically administering to only the patient diagnosed with RRMS and having a EDSS score of greater than 3.0 an amount of laquinimod effective to treat the patient.

The subject invention also provides a method of treating a human patient afflicted with relapsing-remitting multiple sclerosis (RRMS), comprising a) diagnosing the patient as having a baseline disability score according to the Kurtzke Expanded Disability Status Scale (EDSS) of greater than 3.0, and b) administering to the patient an amount of laquinimod effective to treat the patient only if the patient has been diagnosed as having an EDSS score of greater than 3.0.

The subject invention also provides a method of reducing ambulatory deterioration in a human patient diagnosed to be afflicted with relapsing-remitting multiple sclerosis (RRMS) and having a high baseline disability score according to the Kurtzke Expanded Disability Status Scale (EDSS), comprising periodically administering to only the patient diagnosed with RRMS and having a high baseline disability score an amount of laquinimod effective to reduce ambulatory deterioration.

The subject invention also provides a method of reducing ambulatory deterioration in a human patient diagnosed to be afflicted with relapsing-remitting multiple sclerosis (RRMS) and having a baseline disability score according to the Kurtzke Expanded Disability Status Scale (EDSS) of greater than 3.0, comprising periodically administering to only the patient diagnosed with RRMS and having a baseline EDSS of greater than 3.0 an amount of laquinimod effective to reduce ambulatory deterioration.

The subject invention also provides laquinimod for the manufacture of a medicament for use in treating only a human patient diagnosed to be afflicted with relapsing-remitting multiple sclerosis (RRMS) and having a high baseline disability score according to the Kurtzke Expanded Disability Status Scale (EDSS).

The subject invention also provides a pharmaceutical composition comprising an effective amount of laquinimod for treating only a human patient diagnosed to be afflicted with relapsing-remitting multiple sclerosis (RRMS) and having a high baseline disability score according to the Kurtzke Expanded Disability Status Scale (EDSS).

The subject invention also provides a package comprising: a) a pharmaceutical composition comprising an amount of laquinimod; and b) instruction for use of the pharmaceutical composition to treat only a human patient diagnosed to be afflicted with relapsing-remitting multiple sclerosis (RRMS) and having a high baseline disability score according to the Kurtzke Expanded Disability Status Scale (EDSS).

The subject invention also provides a therapeutic package for dispensing to, or for use in dispensing to, only a human patient diagnosed to be afflicted with relapsing-remitting multiple sclerosis (RRMS) and having a high baseline disability score according to the Kurtzke Expanded Disability Status Scale (EDSS), which comprises: a) one or more unit doses, each such unit dose comprising an amount of laquinimod thereof, wherein the amount of said laquinimod in said unit dose is effective, upon administration to said patient, to treat the patient, and b) a finished pharmaceutical container therefor, said container containing said unit dose or unit doses, said container further containing or comprising labeling directing the use of said package in the treatment of said patient.

The subject invention also provides laquinimod for the manufacture of a medicament for use in treating only a human patient diagnosed to be afflicted with relapsing-remitting multiple sclerosis (RRMS) and having a baseline disability score according to the Kurtzke Expanded Disability Status Scale (EDSS) of greater than 3.0.

The subject invention also provides a pharmaceutical composition comprising an effective amount of laquinimod for treating only a human patient diagnosed to be afflicted with relapsing-remitting multiple sclerosis (RRMS) and having a baseline disability score according to the Kurtzke Expanded Disability Status Scale (EDSS) of greater than 3.0.

The subject invention also provides a package comprising: a) a pharmaceutical composition comprising an amount of laquinimod; and b) instruction for use of the pharmaceutical composition to treat only a human patient diagnosed to be afflicted with relapsing-remitting multiple sclerosis (RRMS) and having a baseline disability score according to the Kurtzke Expanded Disability Status Scale (EDSS) of greater than 3.0.

The subject invention also provides a therapeutic package for dispensing to, or for use in dispensing to, only a human patient diagnosed to be afflicted with relapsing-remitting multiple sclerosis (RRMS) and having a baseline disability score according to the Kurtzke Expanded Disability Status Scale (EDSS) of greater than 3.0, which comprises: a) one or more unit doses, each such unit dose comprising an amount of laquinimod thereof, wherein the amount of said laquinimod in said unit dose is effective, upon administration to said patient, to treat the patient, and b) a finished pharmaceutical container therefor, said container containing said unit dose or unit doses, said container further containing or comprising labeling directing the use of said package in the treatment of said patient.

The subject invention also provides a method of treating a human patient diagnosed to be afflicted with RRMS and having impaired mobility, comprising periodically administering to only the patient diagnosed with RRMS and having impaired mobility an amount of laquinimod effective to treat the patient.

The subject invention further provides a method of treating a human patient afflicted with RRMS, comprising a) diagnosing the patient as having mobility impairment as assessed by the patient's Timed-25 foot walk test core, and b) administering to the patient an amount of laquinimod effective to treat the patient only if the patient has been diagnosed as having a mobility impairment.

The subject invention further provides a method of reducing mobility deterioration in a human patient diagnosed to be afflicted with RMS and having impaired mobility, comprising periodically administering to only the patient diagnosed with RRMS and having impaired mobility an amount of laquinimod effective to reduce mobility deterioration.

The subject invention further provides laquinimod for the manufacture of a medicament for use in treating only a human patient diagnosed to be afflicted with RRMS and having impaired mobility.

The subject invention further provides a pharmaceutical composition comprising an effective amount of laquinimod for use in treating only a human patient diagnosed to be afflicted with RRMS and having impaired mobility.

The subject invention further provides a package comprising a) a pharmaceutical composition comprising an amount of laquinimod; and b) instruction for use of the pharmaceutical composition to treat only a human patient diagnosed to be afflicted with RRMS and having impaired mobility.

The subject invention further provides a therapeutic package for dispensing to, or for use in dispensing to, only a human patient diagnosed to be afflicted with RRMS and having impaired mobility, which comprises: a) one or more unit doses, each such unit dose comprising an amount of laquinimod thereof, wherein the amount of said laquinimod in said unit dose is effective, upon administration to said patient, to treat the patient, and b) a finished pharmaceutical container therefor, said container containing said unit dose or unit doses, said container further containing or comprising labeling directing the use of said package in the treatment of said patient.

The subject invention also provides a method of treating a human patient diagnosed to be afflicted with RRMS and having worsening MS, comprising periodically administering to only the patient diagnosed with RRMS and having worsening MS an amount of laquinimod effective to treat the patient.

The subject invention also provides laquinimod for the manufacture of a medicament for use in treating only a human patient diagnosed to be afflicted with relapsing-remitting multiple sclerosis (RRMS) and having worsening MS.

The subject invention also provides a pharmaceutical composition comprising an effective amount of laquinimod for treating only a human patient diagnosed to be afflicted with relapsing-remitting multiple sclerosis (RRMS) and having worsening MS.

The subject invention also provides a package comprising a) a pharmaceutical composition comprising an amount of laquinimod; and b) instruction for use of the pharmaceutical composition to treat only a human patient diagnosed to be afflicted with RRMS and having worsening MS.

The subject invention also provides a therapeutic package for dispensing to, or for use in dispensing to, only a human patient diagnosed to be afflicted with RRMS and having worsening MS, which comprises: a) one or more unit doses, each such unit dose comprising an amount of laquinimod thereof, wherein the amount of said laquinimod in said unit dose is effective, upon administration to said patient, to treat the patient, and b) a finished pharmaceutical container therefor, said container containing said unit dose or unit doses, said container further containing or comprising labeling directing the use of said package in the treatment of said patient.

BRIEF DESCRIPTION OF THE DRAWINGS

FIG. 2: Example 3: Time 25-Foot Walk (T25FW) Results (Mean Change from Baseline to 24 Month) by Treatment in Patients with EDSS>3 who experienced CDP.

DETAILED DESCRIPTION OF THE INVENTION

Figure 1:
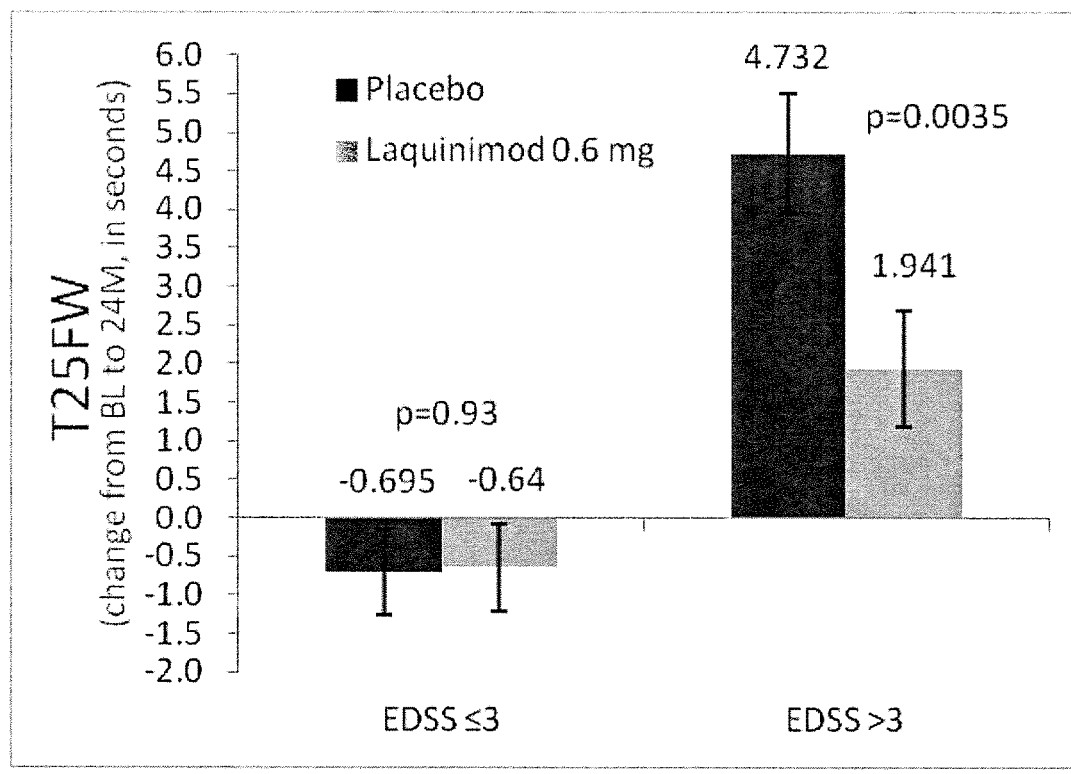
FIG. 1: Example 3: Time 25-Foot Walk (T25FW) Results (Mean Change from Baseline to 24 Months) in the EDSS≤3 Patient group versus the EDSS>3 Patient group.

The subject invention provides a method of treating a human patient diagnosed to be afflicted with relapsing-remitting multiple sclerosis (RRMS) and having a high baseline disability score according to the Kurtzke Expanded Disability Status Scale (EDSS), comprising periodically administering to only the patient diagnosed with RRMS and having a high baseline disability score an amount of laquinimod effective to treat the patient.

The subject invention also provides a method of treating a human patient afflicted with relapsing-remitting multiple sclerosis (RRMS), comprising a) diagnosing the patient as having a high baseline disability score according to the Kurtzke Expanded Disability Status Scale (EDSS), and b) administering to the patient an amount of laquinimod effective to treat the patient only if the patient has been diagnosed as having a high baseline disability score.

In one embodiment, the high baseline disability score is a baseline EDSS score of greater than 3. In another embodiment, the high baseline disability score is a baseline EDSS score of greater than 3.5. In another embodiment, the high baseline disability score is a baseline EDSS score of greater than 4.0. In another embodiment, the high baseline disability score is a baseline EDSS score of greater than 4.5. In another embodiment, the high baseline disability score is a baseline EDSS score of greater than 5.0. In another embodiment, the high baseline disability score is a baseline EDSS score of greater than 5.5.

The subject invention also provides a method of treating a human patient diagnosed to be afflicted with relapsing-remitting multiple sclerosis (RRMS) and having a baseline disability score according to the Kurtzke Expanded Disability Status Scale (EDSS) of greater than 3.0, comprising periodically administering to only the patient diagnosed with RRMS and having a EDSS score of greater than 3.0 an amount of laquinimod effective to treat the patient.

The subject invention also provides a method of treating a human patient afflicted with relapsing-remitting multiple sclerosis (RRMS), comprising a) diagnosing the patient as having a baseline disability score according to the Kurtzke Expanded Disability Status Scale (EDSS) of greater than 3.0, and b) administering to the patient an amount of laquinimod effective to treat the patient only if the patient has been diagnosed as having an EDSS score of greater than 3.0.

In one embodiment, the amount of laquinimod is effective to reduce the patient's relapse rate. In another embodiment, the amount of laquinimod is effective to reduce the patient's accumulation of physical disability.

In an embodiment, the accumulation of physical disability is assessed by the patient's Multiple Sclerosis Functional Composite (MSFC) score. In another embodiment, the amount of laquinimod is effective to reduce deterioration of the patient's ambulation. In another embodiment, ambulation is assessed by the patient's Timed-25 foot walk test score. In another embodiment, after 24 months of periodic administration of laquinimod, the patient's accumulation of physical disability is reduced as compared to a patient not receiving periodic administration of laquinimod.

In an embodiment, the accumulation of physical disability is assessed by the time to confirmed disease progression (CDP) as measured by EDSS score. In another embodiment, the patient has a baseline EDSS score of 3.5-5.0 and CDP is a 1 point increase of the baseline EDSS score. In another embodiment, the patient has a baseline EDSS score of greater than 3.5, and CDP is a 1 point increase of the baseline EDSS score. In another embodiment, the patient has a baseline EDSS score of greater than 4.0, and CDP is a 1 point increase of the baseline EDSS score. In another embodiment, the patient has a baseline EDSS score of greater than 4.5, and CDP is a 1 point increase of the baseline EDSS score. In another embodiment, the patient has a baseline EDSS score of greater than 5.0, and CDP is a 1 point increase of the baseline EDSS score. In another embodiment, the patient has a baseline EDSS score of greater than 5.5, and CDP is a 1 point increase of the baseline EDSS score. In another embodiment, the patient has a baseline EDSS score of 5.5 or greater and CDP is a 0.5 point increase of the baseline EDSS score.

In one embodiment, CDP is sustained for at least 3 months. In another embodiment, CDP is sustained for at least 6 months.

The subject invention also provides a method of reducing ambulatory deterioration in a human patient diagnosed to be afflicted with relapsing-remitting multiple sclerosis (RRMS) and having a high baseline disability score according to the Kurtzke Expanded Disability Status Scale (EDSS), comprising periodically administering to only the patient diagnosed with RRMS and having a high baseline disability score an amount of laquinimod effective to reduce ambulatory deterioration. In an embodiment, the high baseline disability score is a baseline EDSS score of greater than 3.

The subject invention also provides a method of reducing ambulatory deterioration in a human patient diagnosed to be afflicted with relapsing-remitting multiple sclerosis (RRMS) and having a baseline disability score according to the Kurtzke Expanded Disability Status Scale (EDSS) of greater than 3.0, comprising periodically administering to only the patient diagnosed with RRMS and having a baseline EDSS of greater than 3.0 an amount of laquinimod effective to reduce ambulatory deterioration.

In one embodiment, ambulation is assessed by the patient's Timed-25 foot walk test score. In another embodiment, after 24 months of periodic administration of laquinimod, deterioration of the patient's ambulation is reduced as compared to a patient not receiving periodic administration of laquinimod.

In an embodiment, the patient has been diagnosed with a baseline EDSS score of greater than 3.5. In another embodiment, the patient has been diagnosed with a baseline EDSS score of greater than 4.0. In another embodiment, the patient has been diagnosed with a baseline EDSS score of greater than 4.5. In another embodiment, the patient has been diagnosed with a baseline EDSS score of greater than 5.0. In another embodiment, the patient has been diagnosed with a baseline EDSS score of greater than 5.5. In yet another embodiment, the patient has been diagnosed with a baseline EDSS score of 3.5-5.5.

In one embodiment, the patient is naïve to an RRMS treatment. In another embodiment, the patient is naïve to any RRMS treatment. In another embodiment, the patient is naïve to laquinimod treatment. In another embodiment, the patient is naïve to 0.3 mg/day laquinimod treatment. In another embodiment, the patient is naïve to 0.6 mg/day laquinimod treatment. In another embodiment, the patient is naïve to 1.2 mg/day laquinimod treatment.

In one embodiment, laquinimod is laquinimod sodium. In another embodiment, laquinimod is administered orally. In another embodiment, laquinimod is administered daily.

In one embodiment, laquinimod is administered at a daily dose of 0.1-2.5 mg laquinimod. In another embodiment of the present invention, the amount laquinimod administered is 0.25 mg/day. In another embodiment, the amount laquinimod administered is 0.3 mg/day. In another embodiment, the amount laquinimod administered is 0.5 mg/day. In another embodiment, the amount laquinimod administered is 0.6 mg/day. In another embodiment, the amount laquinimod administered is 0.9 mg/day. In another embodiment, the amount laquinimod administered is 1.0 mg/day. In another embodiment, the amount laquinimod administered is 1.2 mg/day. In another embodiment, the amount laquinimod administered is 1.5 mg/day. In another embodiment, the amount laquinimod administered is 1.8 mg/day. In another embodiment, the amount laquinimod administered is 2.0 mg/day. In another embodiment, the amount laquinimod administered is 2.5 mg/day. In yet another embodiment, the amount of laquinimod administered is about the amounts disclosed above.

In one embodiment, the periodic administration is for a period of greater than 24 weeks. In another embodiment, laquinimod is administered as monotherapy for RRMS. In another embodiment, laquinimod is administered as adjunct therapy with an other RRMS treatment. In another embodiment, the other RRMS treatment is administration of interferon beta 1-a, interferon beta 1-b, glatiramer acetate, mitoxantrone or natalizumab.

The subject invention also provides laquinimod for the manufacture of a medicament for use in treating only a human patient diagnosed to be afflicted with relapsing-remitting multiple sclerosis (RRMS) and having a high baseline disability score according to the Kurtzke Expanded Disability Status Scale (EDSS). In an embodiment, the high baseline disability score is a baseline EDSS score of greater than 3.

The subject invention also provides a pharmaceutical composition comprising an effective amount of laquinimod for treating only a human patient diagnosed to be afflicted with relapsing-remitting multiple sclerosis (RRMS) and having a high baseline disability score according to the Kurtzke Expanded Disability Status Scale (EDSS). In an embodiment, the high baseline disability score is a baseline EDSS score of greater than 3.

The subject invention also provides a package comprising: a) a pharmaceutical composition comprising an amount of laquinimod; and b) instruction for use of the pharmaceutical composition to treat only a human patient diagnosed to be afflicted with relapsing-remitting multiple sclerosis (RRMS) and having a high baseline disability score according to the Kurtzke Expanded Disability Status Scale (EDSS). In an embodiment, the high baseline disability score is a baseline EDSS score of greater than 3.

The subject invention also provides a therapeutic package for dispensing to, or for use in dispensing to, only a human patient diagnosed to be afflicted with relapsing-remitting multiple sclerosis (RRMS) and having a high baseline disability score according to the Kurtzke Expanded Disability Status Scale (EDSS), which comprises: a) one or more unit doses, each such unit dose comprising an amount of laquinimod thereof, wherein the amount of said laquinimod in said unit dose is effective, upon administration to said patient, to treat the patient, and b) a finished pharmaceutical container therefor, said container containing said unit dose or unit doses, said container further containing or comprising labeling directing the use of said package in the treatment of said patient. In an embodiment, the high baseline disability score is a baseline EDSS score of greater than 3.

The subject invention also provides laquinimod for the manufacture of a medicament for use in treating only a human patient diagnosed to be afflicted with relapsing-remitting multiple sclerosis (RRMS) and having a baseline disability score according to the Kurtzke Expanded Disability Status Scale (EDSS) of greater than 3.0.

The subject invention also provides a pharmaceutical composition comprising an effective amount of laquinimod for treating only a human patient diagnosed to be afflicted with relapsing-remitting multiple sclerosis (RRMS) and having a baseline disability score according to the Kurtzke Expanded Disability Status Scale (EDSS) of greater than 3.0.

The subject invention also provides a package comprising: a) a pharmaceutical composition comprising an amount of laquinimod; and b) instruction for use of the pharmaceutical composition to treat only a human patient diagnosed to be afflicted with relapsing-remitting multiple sclerosis (RRMS) and having a baseline disability score according to the Kurtzke Expanded Disability Status Scale (EDSS) of greater than 3.0.

The subject invention also provides a therapeutic package for dispensing to, or for use in dispensing to, only a human patient diagnosed to be afflicted with relapsing-remitting multiple sclerosis (RRMS) and having a baseline disability score according to the Kurtzke Expanded Disability Status Scale (EDSS) of greater than 3.0, which comprises: a) one or more unit doses, each such unit dose comprising an amount of laquinimod thereof, wherein the amount of said laquinimod in said unit dose is effective, upon administration to said patient, to treat the patient, and b) a finished pharmaceutical container therefor, said container containing said unit dose or unit doses, said container further containing or comprising labeling directing the use of said package in the treatment of said patient.

The subject invention also provides laquinimod for the manufacture of a medicament for use in reducing ambulatory deterioration only in a human patient diagnosed to be afflicted with relapsing-remitting multiple sclerosis (RRMS) and having a high baseline disability score according to the Kurtzke Expanded Disability Status Scale (EDSS). In an embodiment, the high baseline disability score is a baseline EDSS score of greater than 3.

The subject invention also provides a pharmaceutical composition comprising an effective amount of laquinimod for reducing ambulatory deterioration only in a human patient diagnosed to be afflicted with relapsing-remitting multiple sclerosis (RRMS) and having a high baseline disability score according to the Kurtzke Expanded Disability Status Scale (EDSS). In an embodiment, the high baseline disability score is a baseline EDSS score of greater than 3.

The subject invention also provides a package comprising: a) a pharmaceutical composition comprising an amount of laquinimod; and b) instruction for use of the pharmaceutical composition to reduce ambulatory deterioration only in a human patient diagnosed to be afflicted with relapsing-remitting multiple sclerosis (RRMS) and having a high baseline disability score according to the Kurtzke Expanded Disability Status Scale (EDSS). In an embodiment, the high baseline disability score is a baseline EDSS score of greater than 3.

The subject invention also provides a therapeutic package for dispensing to, or for use in dispensing to, only a human patient diagnosed to be afflicted with relapsing-remitting multiple sclerosis (RRMS) and having a high baseline disability score according to the Kurtzke Expanded Disability Status Scale (EDSS), which comprises: a) one or more unit doses, each such unit dose comprising an amount of laquinimod thereof, wherein the amount of said laquinimod in said unit dose is effective, upon administration to said patient, to reduce ambulatory deterioration in the patient, and b) a finished pharmaceutical container therefor, said container containing said unit dose or unit doses, said container further containing or comprising labeling directing the use of said package in the treatment of said patient. In an embodiment, the high baseline disability score is a baseline EDSS score of greater than 3.

The subject invention also provides a method of treating a human patient diagnosed to be afflicted with RRMS and having impaired mobility, comprising periodically administering to only the patient diagnosed with RRMS and having impaired mobility an amount of laquinimod effective to treat the patient. In an embodiment, mobility is assessed by the patient's Timed-25 foot walk test score.

In an embodiment, the mobility impairment is an ambulatory impairment. In another embodiment, the patient is not ambulatory.

In another embodiment, mobility is assessed by the MSWS-12 self-report questionnaire. In another embodiment, mobility is assessed by the Ambulation Index. In another embodiment, mobility is assessed by the Six-Minute Walk (6MW) Test. In yet another embodiment, mobility is assessed by the LEMMT Test.

The subject invention also provides a method of treating a human patient afflicted with RRMS, comprising a) diagnosing the patient as having a mobility impairment as assessed by the patient's Timed-25 foot walk test score, and b) administering to the patient an amount of laquinimod effective to treat the patient only if the patient has been diagnosed as having a mobility impairment.

In an embodiment, the mobility impairment is an ambulatory impairment. In another embodiment, the patient is not ambulatory.

In one embodiment, the amount of laquinimod is effective to reduce the patient's relapse rate. In another embodiment, the amount of laquinimod is effective to reduce the patient's accumulation of physical disability.

In one embodiment, the accumulation of physical disability is assessed by the patient's MSFC score. In another embodiment, the amount of laquinimod is effective to reduce deterioration of the patient's ambulation. In another embodiment, after 24 months of periodic administration of laquinimod, the patient's accumulation of physical disability is reduced as compared to a patient not receiving periodic administration of laquinimod. In another embodiment, the accumulation of physical disability is assessed by the time to CDP as measured by EDSS score. In another embodiment, the patient has a baseline EDSS score of 3.5-5.0 and CDP is a 1 point increase of the baseline EDSS score. In another embodiment, the patient has a baseline EDSS score of greater than 3.5, greater than 4.0, greater than 4.5, greater than 5.0, or greater than 5.5, and CDP is a 1 point increase of the baseline EDSS score. In another embodiment, the patient has a baseline EDSS score of 5.5 or greater and CDP is a 0.5 point increase of the baseline EDSS score.

In one embodiment, CDP is sustained for at least 3 months. In another embodiment, CDP is sustained for at least 6 months.

The subject invention also provides a method of reducing mobility deterioration in a human patient diagnosed to be afflicted with RRMS and having impaired mobility, comprising periodically administering to only the patient diagnosed with RRMS and having impaired mobility an amount of laquinimod effective to reduce mobility deterioration.

In an embodiment, the mobility impairment is an ambulatory impairment. In another embodiment, the patient is not ambulatory.

In an embodiment, mobility is assessed by the patient's Timed-25 foot walk test score.

In one embodiment, after 24 months of periodic administration of laquinimod, deterioration of the patient's mobility is reduced as compared to a patient not receiving periodic administration of laquinimod. In another embodiment, the patient has been diagnosed with a baseline EDSS score of greater than 3.5, greater than 4.0, greater than 4.5, greater than 5.0, or greater than 5.5. In another embodiment, the patient has been diagnosed with a baseline EDSS score of 3.5-5.5.

In one embodiment, the patient is naïve to an RRMS treatment. In another embodiment, the patient is naïve to laquinimod treatment. In another embodiment, the patient is naïve to 0.3 mg/day laquinimod treatment. In another embodiment, the patient is naïve to 0.6 mg/day laquinimod treatment. In another embodiment, the patient is naïve to 1.2 mg/day laquinimod treatment.

In an embodiment, laquinimod is laquinimod sodium. In another embodiment, laquinimod is administered orally. In another embodiment, laquinimod is administered daily. In another embodiment, laquinimod is administered at a daily dose of 0.1-2.5 mg laquinimod. In another embodiment, laquinimod is administered at a daily dose of 0.6 mg laquinimod. In another embodiment, the periodic administration is for a period of greater than 24 weeks.

In one embodiment, laquinimod is administered as monotherapy for RRMS. In another embodiment, laquinimod is administered as adjunct therapy with an other RRMS treatment. In another embodiment, the other RRMS treatment is administration of interferon beta 1-a, interferon beta 1-b, glatiramer acetate, mitoxantrone or natalizumab.

The subject invention also provides laquinimod for the manufacture of a medicament for use in treating only a human patient diagnosed to be afflicted with RRMS and having impaired mobility.

In an embodiment, the mobility impairment is an ambulatory impairment. In another embodiment, the patient is not ambulatory.

The subject invention also provides a pharmaceutical composition comprising an effective amount of laquinimod for use in treating only a human patient diagnosed to be afflicted with RRMS and having impaired mobility.

In an embodiment, the mobility impairment is an ambulatory impairment. In another embodiment, the patient is not ambulatory.

In one embodiment, mobility is assessed by the patient's Timed-25 foot walk test score.

The subject invention also provides a package comprising: a) a pharmaceutical composition comprising an amount of laquinimod; and b) instruction for use of the pharmaceutical composition to treat only a human patient diagnosed to be afflicted with RRMS and having impaired mobility.

The subject invention also provides a therapeutic package for dispensing to, or for use in dispensing to, only a human patient diagnosed to be afflicted with RRMS and having impaired mobility, which comprises: a) one or more unit doses, each such unit dose comprising an amount of laquinimod thereof, wherein the amount of said laquinimod in said unit dose is effective, upon administration to said patient, to treat the patient, and b) a finished pharmaceutical container therefor, said container containing said unit dose or unit doses, said container further containing or comprising labeling directing the use of said package in the treatment of said patient.

In one embodiment of the package or the therapeutic package as described herein, the mobility impairment is an ambulatory impairment. In another embodiment, the patient is not ambulatory. In another embodiment, the patient's mobility is assessed by the patient's Timed-25 foot walk test score.

The subject invention also provides a method of treating a human patient diagnosed to be afflicted with RRMS and having worsening MS, comprising periodically administering to only the patient diagnosed with RRMS and having worsening MS an amount of laquinimod effective to treat the patient. In an embodiment, the patient has a baseline disability score according to the Kurtzke Expanded Disability Status Scale (EDSS) of greater than 3.0. In one embodiment, laquinimod is laquinimod sodium. In another embodiment, laquinimod is administered orally. In another embodiment, laquinimod is administered daily. In another embodiment, laquinimod is administered at a daily dose of 0.1-2.5 mg laquinimod. In another embodiment, laquinimod is administered at a daily dose of 0.6 mg laquinimod. In another embodiment, laquinimod is administered at a daily dose of 1.2 mg laquinimod.

In one embodiment, laquinimod is administered as monotherapy for RRMS. In another embodiment, laquinimod is administered as adjunct therapy with another RRMS treatment. In another embodiment, the other RRMS treatment is administration of interferon beta 1-a, interferon beta 1-b, glatiramer acetate, mitoxantrone or natalizumab.

The subject invention also provides laquinimod for the manufacture of a medicament for use in treating only a human patient diagnosed to be afflicted with relapsing-remitting multiple sclerosis (RRMS) and having worsening MS.

The subject invention also provides a pharmaceutical composition comprising an effective amount of laquinimod for treating only a human patient diagnosed to be afflicted with relapsing-remitting multiple sclerosis (RRMS) and having worsening MS. In an embodiment of the use of laquinimod or pharmaceutical composition, the patient has a baseline disability score according to the Kurtzke Expanded Disability Status Scale (EDSS) of greater than 3.0.

The subject invention also provides a package comprising: a) a pharmaceutical composition comprising an amount of laquinimod; and b) instruction for use of the pharmaceutical composition to treat only a human patient diagnosed to be afflicted with RRMS and having worsening MS.

The subject invention also provides a therapeutic package for dispensing to, or for use in dispensing to, only a human patient diagnosed to be afflicted with RRMS and having worsening MS, which comprises: a) one or more unit doses, each such unit dose comprising an amount of laquinimod thereof, wherein the amount of said laquinimod in said unit dose is effective, upon administration to said patient, to treat the patient, and b) a finished pharmaceutical container therefor, said container containing said unit dose or unit doses, said container further containing or comprising labeling directing the use of said package in the treatment of said patient.

For the foregoing embodiments, each embodiment disclosed herein is contemplated as being applicable to each of the other disclosed embodiment.

A dosage unit may comprise a single compound or mixtures of compounds thereof. A dosage unit can be prepared for oral dosage forms, such as tablets, capsules, pills, powders, and granules.

Laquinimod can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit may in a form suitable for oral administration. Laquinimod can be administered alone but is generally mixed with a pharmaceutically acceptable carrier, and co-administered in the form of a tablet or capsule, liposome, or as an agglomerated powder. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents flow-inducing agents, and melting agents.

Specific examples of the techniques, pharmaceutically acceptable carriers and excipients that may be used to formulate oral dosage forms of the present invention are described, e.g., in U.S. Patent Application Publication No. 2005/0192315, PCT International Application Publication Nos. WO 2005/074899, WO 2007/047863, and 2007/146248.

General techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol. 40 (Gilbert S. Banker, Christopher T. Rhodes, Eds.). These references in their entireties are hereby incorporated by reference into this application.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, dicalcium phosphate, calcium sulfate, mannitol, sorbitol, microcrystalline cellulose and the like. Suitable binders include starch, gelatin, natural sugars such as glucose or beta-lactose, corn starch, natural and synthetic gums such as acacia, tragacanth, or sodium alginate, povidone, carboxymethylcellulose, polyethylene glycol, waxes, and the like. Lubricants used in these dosage forms include sodium oleate, sodium stearate, sodium benzoate, sodium acetate, sodium chloride, stearic acid, sodium stearyl fumarate, talc and the like. Disintegrators include, without limitation, starch, methyl cellulose, agar, bentonite, xanthan gum, croscarmellose sodium, sodium starch glycolate and the like.

TERMS

As used herein, and unless stated otherwise, each of the following terms shall have the definition set forth below.

As used herein, "laquinimod" means laquinimod acid or a pharmaceutically acceptable salt thereof. A "pharmaceutically acceptable salt" of laquinimod as used in this application includes lithium, sodium, potassium, magnesium, calcium, manganese, copper, zinc, aluminum and iron. Salt formulations of laquinimod and the process for preparing the same are described, e.g., in U.S. Patent Application Publication No. 2005/0192315 and PCT International Application Publication No. WO 2005/074899, which are hereby incorporated by reference into this application.

As used herein, an "amount" or "dose" of laquinimod as measured in milligrams refers to the milligrams of laquinimod acid present in a preparation, regardless of the form of the preparation. A "dose of 0.6 mg laquinimod" means the amount of laquinimod acid in a preparation is 0.6 mg, regardless of the form of the preparation. Thus, when in the form of a salt, e.g. a laquinimod sodium salt, the weight of the salt form necessary to provide a dose of 0.6 mg laquinimod would be greater than 0.6 mg (e.g., 0.64 mg) due to the presence of the additional salt ion.

As used herein, "about" in the context of a numerical value or range means±10% of the numerical value or range recited or claimed.

As used herein, a "unit dose", "unit doses" and "unit dosage form(s)" mean a single drug administration entity/entities.

As used herein, a subject at "baseline" is as subject prior to administration of laquinimod in a therapy as described herein.

As used herein, a subject who is "naïve" to a particular therapy is a subject who has not previously received said therapy.

As used herein, a human patient "diagnosed to be afflicted with relapsing-remitting multiple sclerosis" means a human patient who has been clinically diagnosed to have relapsing-remitting multiple sclerosis. As used herein, "Relapsing-Remitting Multiple Sclerosis" or "RRMS" is characterized by clearly defined acute attacks with full recovery or with sequelae and residual deficit upon recovery (Lublin, 1996) Relapsing-remitting multiple sclerosis can be diagnosed, e.g., as defined by the Revised McDonald Criteria (Polman 2011).

As used herein, a human patient "diagnosed to have" a high baseline disability score according to the Kurtzke Expanded Disability Status Scale (EDSS), means a human patient who has been clinically diagnosed to have "a high baseline disability score", which, as used herein, means a baseline EDSS score of ≥3, >3, ≥3.5, >3.5, ≥4, >4, ≥4.5, >4.5, ≥5, >5, ≥5.5, or >5.5. Similarly, as used herein, a human patient "diagnosed to have" a baseline disability score according to the Kurtzke Expanded Disability Status Scale (EDSS) of greater than 3.0 means a human patient who has been clinically diagnosed to have a baseline EDSS score of >3.

As used herein, "administering to a/the human patient" means the giving of, dispensing of, or application of medicines, drugs, or remedies to the human patient to relieve, cure, or reduce the symptoms associated with a disease, disorder or condition, e.g., a pathological condition. As used herein, "administering only to a/the human patient . . . " means the giving of, dispensing of, or application of medicines, drugs, or remedies to only the human patient population identified to the exclusion of all other potential patient populations. The administration can be periodic administration. As used herein, "periodic administration" means repeated/recurrent administration separated by a period of time. The period of time between administrations is preferably consistent from time to time. Periodic administration can include administration, e.g., once daily, twice daily, three times daily, four times daily, weekly, twice weekly, three times weekly, four times weekly and so on, etc.

As used herein, "treating" (or treat) encompasses, e.g., inducing inhibition, regression, or stasis of a disease or disorder, or lessening, suppressing, inhibiting, reducing the severity of, eliminating or substantially eliminating, or ameliorating a symptom of the disease or disorder. As used herein, "inhibition" of disease progression or disease complication in a subject means preventing or reducing the disease progression and/or disease complication in the subject.

A "symptom" associated with a disease or disorder includes any clinical or laboratory manifestation associated with the disease or disorder and is not limited to what the subject can feel or observe.

As used herein, "effective" when referring to an amount of laquinimod refers to the quantity of laquinimod that is sufficient to yield a desired therapeutic response without undue adverse side effects (such as toxicity, irritation, or allergic response) commensurate with a reasonable benefit/risk ratio when used in the manner of this invention.

As used herein, "Confirmed Relapse" is defined as the appearance of one or more new neurological abnormalities or the reappearance of one or more previously observed neurological abnormalities wherein the change in clinical state lasts at least 48 hours and is immediately preceded by an improving neurological state of at least thirty (30) days from onset of previous relapse. This criterion is different from the clinical definition of relapse which requires only 24 hours duration of symptoms. (EMEA Guideline, 2006) Since "in study" relapse definition must be supported by an objective neurological evaluation as discussed below, a neurological deficit must sustain long enough to eliminate pseudo-relapses.

An event is a relapse only when the subject's symptoms are accompanied by observed objective neurological changes, consistent with at least one of the following: an increase of at least 0.5 in the EDSS score as compared to the previous evaluation, an increase of one grade in the score of 2 or more of the 7 FS functions as compared to the previous evaluation, or an increase of 2 grades in the score of one FS as compared to the previous evaluation.

In addition, the subject must not be undergoing any acute metabolic changes such as fever or other medical abnormality. A change in bowel/bladder function or in cognitive function must not be entirely responsible for the changes in EDSS or FS scores.

As used herein, "Relapse Rate" is the number of confirmed relapses per unit time. "Annualized relapse rate" or "ARR" is the mean value of the number of confirmed relapses of each patient multiplied by 365 and divided by the number of days that patient is on the study drug.

As used herein, "Expanded Disability Status Scale" or "EDSS" is a rating system that is frequently used for classifying and standardizing the condition of people with multiple sclerosis. The score ranges from 0.0 representing a normal neurological exam to 10.0 representing death due to MS. The score is based upon neurological testing and examination of functional systems (FS), which are areas of the central nervous system which control bodily functions. The functional systems are: Pyramidal (ability to walk), Cerebellar (coordination), Brain stem (speech and swallowing), Sensory (touch and pain), Bowel and bladder functions, Visual, Mental, and Other (includes any other neurological findings due to MS). (Kurtzke J F, 1983)

As used herein, a "confirmed progression" of EDSS, or "confirmed disease progression" as measured by EDSS score is defined as a 1 point increase from baseline EDSS if baseline EDSS was between 0 and 5.0, or a 0.5 point increase if baseline EDSS was 5.5. In order to be considered a confirmed progression, the change (either 1 point or 0.5 points) must be sustained for at least 3 months. In addition, confirmation of progression cannot be made during a relapse.

As used herein, an "adverse event" or "AE" means any untoward medical occurrence in a clinical trial subject administered a medicinal product and which does not have a causal relationship with the treatment. An adverse event can therefore be any unfavorable and unintended sign including an abnormal laboratory finding, symptom, or diseases temporally associated with the use of an investigational medicinal product, whether or not considered related to the investigational medicinal product.

As used herein, "Ambulation Index" or "AI" is a rating scale developed by Hauser et al. to assess mobility by evaluating the time and degree of assistance required to walk 25 feet. Scores range from 0 (asymptomatic and fully active) to 10 (bedridden). The patient is asked to walk a marked 25-foot course as quickly and safely as possible. The examiner records the time and type of assistance (e.g., cane, walker, crutches) needed. (Hauser, 1983)

As used herein "mobility" refers to any ability relating to walking/ambulation, walking speed, gait, strength of leg muscles, leg function and the ability to move with or without assistance. Mobility can be evaluated by one or more of several tests including but not limited to Ambulation Index, Timed 25 foot walk, Six-Minute Walk (6MW), Lower Extremity Manual Muscle Test (LEMMT), and EDSS. Mobility can also be reported by the subject, for example by questionnaires, including but not limited to 12-Item Multiple Sclerosis Walking Scale (MSWS-12). "Impaired Mobility" as used herein refers to any impairment, difficulty or disability relating to mobility.

The "Six-Minute Walk (6MW) Test" is a commonly used test developed to assess exercise capacity in patients with COPD (Guyatt, 1985). It has been used also to measure mobility in multiple sclerosis patients (Clinical Trials Website).

The "Timed-25 Foot Walk" or "T25-FW" is a quantitative mobility and leg function performance test based on a timed 25-walk. The patient is directed to one end of a clearly marked 25-foot course and is instructed to walk 25 feet as quickly as possible, but safely. The time is calculated from the initiation of the instruction to start and ends when the patient has reached the 25-foot mark. The task is immediately administered again by having the patient walk back the same distance. Patients may use assistive devices when doing this task. The score for the T25-FW is the average of the two completed trials. This score can be used individually or used as part of the MSFC composite score (National MS Society Website).

As used herein, "EQ-5D" is a standardized questionnaire instrument for use as a measure of health outcome applicable to a range of health conditions and treatments. It provides a simple descriptive profile and a single index value for health status that can be used in the clinical and economic evaluation of health care as well as population health surveys. EQ-5D was developed by the "EuroQoL" Group which comprises a network of international, multi-lingual, multidisciplinary researchers, originally from seven centers in England, Finland, the Netherlands, Norway and Sweden. The EQ-5D questionnaire is in the public domain and can be obtained from EuroQoL.

As used herein, "Gd-enhancing lesion" refers to lesions that result from a breakdown of the blood-brain barrier, which appear in contrast studies using gadolinium contrast agents. Gadolinium enhancement provides information as to the age of a lesion, as Gd-enhancing lesions typically occur within a six week period of lesion formation.

As used herein, "Magnetization Transfer Imaging" or "MTI" is based on the magnetization interaction (through dipolar and/or chemical exchange) between bulk water protons and macromolecular protons. By applying an off resonance radio frequency pulse to the macromolecular protons, the saturation of these protons is then transferred to the bulk water protons. The result is a decrease in signal (the net magnetization of visible protons is reduced), depending on the magnitude of MT between tissue macromolecules and bulk water. "MT" or "Magnetization Transfer" refers to the transfer of longitudinal magnetization from the hydrogen nuclei of water that have restricted motion to the hydrogen nuclei of water that moves with many degrees of freedom. With MTI, the presence or absence of macromolecules (e.g. in membranes or brain tissue) can be seen. (Mehta, 1996; Grossman, 1994)

As used herein, "Magnetization Resonance Spectroscopy" or "MRS" is a specialized technique associated with magnetic resonance imaging (MRI). MRS is used to measure the levels of different metabolites in body tissues. The MR signal produces a spectrum of resonances that correspond to different molecular arrangements of the isotope being "excited". This signature is used to diagnose certain metabolic disorders, especially those affecting the brain, (Rosen, 2007) as well as to provide information on tumor metabolism. (Golder, 2007)

As used herein, "Modified Fatigue Impact Scale" or "MFIS" is a validated specific subject-reported outcome measure developed to evaluate the impact of fatigue on the lives of people with MS. This instrument provides an assessment of the effects of fatigue in terms of physical, cognitive, and psychosocial functioning. The full-length MFIS consists of 21 items while the abbreviated version has 5 items. (Fisk et al, 1994)

As used herein, "MS Functional Composite" or "MSFC" is a clinical outcome measure for MS. The MSFC comprises quantitative functional measures of three key clinical dimensions of MS: leg function/ambulation, arm/hand function, and cognitive function. Scores on component measures are converted to standard scores (z-scores), which are averaged to form a single MSFC score. (Fischer, 1999)

As used herein, "SF-36" is a multi-purpose, short-form health survey with 36 questions which yields an 8-scale profile of functional health and well-being scores as well as psychometrically-based physical and mental health summary measures and a preference-based health utility index. It is a generic measure, as opposed to one that targets a specific age, disease, or treatment group. The survey is developed by and can be obtained from QualityMetric, Inc. of Providence, R.I.

As used herein, "T1-weighted MRI image" refers to an MR-image that emphasizes T1 contrast by which lesions may be visualized. Abnormal areas in a T1-weighted MRI image are "hypointense" and appear as dark spots. These spots are generally older lesions.

"T2-weighted MRI image" refers to an MR-image that emphasizes T2 contrast by which lesions may be visualized. T2 lesions represent new inflammatory activity.

As used herein, a "pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compounds to the subject.

It is understood that where a parameter range is provided, all integers within that range, and tenths thereof, are also provided by the invention. For example, "0.1-2.5 mg" includes 0.1 mg, 0.2 mg, 0.3 mg, 0.4 mg, 0.5 mg etc. up to 2.5 mg.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1

Clinical Trial (Phase III)—Assessment of Oral Laquinimod in Preventing Progression of MS A multinational (24 countries), multicenter (approximately 139 sites), randomized, double-blinded, parallel-group, placebo-controlled clinical trial ("ALLEGRO" or MS-LAQ-301) was conducted to evaluate the efficacy, safety and tolerability of daily oral administration of laquinimod 0.6 mg in subjects with relapsing remitting multiple sclerosis (RRMS) for a 24 months duration.

One thousand one hundred and six (1106) patients were equally randomized to either laquinimod 0.6 mg or placebo and treated in a double-blind manner and baseline characteristics were balanced between groups. The primary endpoint of the study was the number of confirmed relapses during the double-blind treatment period, which corresponds to the annualized relapse rate (ARR—number of relapses divided by total exposure of all patients). Secondary endpoints included disability as measured by Expanded Disability Status Scale (EDSS) changes confirmed at 3 months, and cumulative number of gadolinium enhancing (GdE) and new/enlarging T2 MRI lesions.

Study Duration

Screening Phase: 1 Month.

Double blind treatment phase: 24 months of once-daily oral administration of daily dose of 0.6 mg laquinimod or matching placebo.

Upon blinded variance and power reassessment of the population progression (planned prior to first subject completes the 20 months of treatment), the double blind study duration may be extended to 30 months. This is planned in order to enhance the statistical power to detect the effect of laquinimod on disability accumulation. The recommendation to extend the study duration is based on a pre-defined rule.

Study Design

Eligible subjects were equally randomized 1:1 into one of the following treatment arms:

1. Laquinimod capsules 0.6 mg: One 0.6 mg laquinimod capsule was administered orally once daily. The 0.6 mg laquinimod capsules contain 0.6 mg of Laquinimod Acid per capsule with meglumine, and were manufactured according to the method disclosed in PCT International Application Publication No. WO/2007/146248, published Dec. 21, 2007 (see, page 10, line 5 to page 11, line 3).
2. Matching placebo for laquinimod arm: one capsule is administered once daily.

Subjects were evaluated at study sites for 12 scheduled visits of the double blind phase at months: −1 (screening), 0 (baseline), 1, 2, 3, 6, 9, 12, 15, 18, 21 and 24 (termination/early discontinuation). In case of the 6 months extended study, subjects were evaluated at study sites at months 27 and 30 (termination/early discontinuation of extended study), in this case month 24 was a regular scheduled visit.

EDSS was assessed every 3 months, MSFC every 6 months, and MRI was performed annually in all patients. A subgroup of patients (n=189) underwent additional MRI scans at months 3 and 6. Subjects successfully completing the study were offered the opportunity to enter into a 1-year open label extension. Patients who discontinued the study underwent a final termination visit and were not further evaluated, except for those who discontinued due to adverse events.

The following assessments were performed at specified time points:

1. Vital signs were measured at each study visit.
2. A physical examination is performed at months −1 (screening), 0 (baseline) 1, 3, 6, 12, 18 and 24 (termination/early discontinuation core study). In case of the 6 months extended study, additional examination was performed at month 30 (termination/early discontinuation of extended study).
3. The following safety clinical laboratory tests were performed:
   a. Complete blood count (CBC) with differential—at all scheduled visits. A reticulocyte count was added to the CBC at months 0 (baseline) and 24/30 (termination/early discontinuation).
   b. Serum chemistry (including electrolytes, liver enzymes, direct and total bilirubin and pancreatic amylase and CPK), and urinalysis—at all scheduled visits.
   c. A rapid urine β-hCG test was performed in women of child-bearing potential at baseline (month 0) and at each scheduled study visit thereafter (at site).
   d. β-hCG in women of child-bearing potential was performed at all scheduled visits.
   e. Starting after visit Month 3 a rapid urine β-hCG test was performed in women of child-bearing potential every 28 (±2) days. The subject was contacted by telephone within 72 hours after the test was scheduled to be performed and asked specific questions regarding the test. In case of suspected pregnancy (positive urine β-hCG test result), the caller made sure that the study drug has been discontinued and the subject was instructed to arrive at the site as soon as possible with all study drugs.
4. Markers of inflammation (serum conventional C-reactive protein and fibrinogen)—at screening, baseline and all scheduled visits thereafter.
5. During the first 3 months periodical phone calls were placed by the site personnel every two weeks. A list of predefined questions relating to signs/symptoms suggestive of vascular thrombosis was presented to the subjects.
6. ECG was performed at months −1 (screening; additional recording, up to 30 minutes apart is performed if $QT_c$ is less than 450 msec), (baseline; three recordings, 15 minutes apart), 1, 2, 3, 6, 12, 18 and 24 (termination/early discontinuation). In case of the 6 months extended study, ECG is performed at month 30 (termination/early discontinuation of the extended study).
7. Chest X-ray is performed at months −1 (screening), (if not performed within 7 months prior to the screening visit).
8. Adverse Events (AEs) are monitored throughout the study.
9. Concomitant medications are monitored throughout the study.
10. Neurological evaluations, including Expanded Disability Status Scale (EDSS), 25 foot walk test/Ambulation Index (AI), Functional systems (FS) are performed at months −1 (screening), 0 (baseline) and every 3 months during the study and the extended study period.
11. MS functional Composite (MSFC) was assessed at months −1 (screening) (three practices for training purposes only), at month 0 (baseline), 6, 12, 18 and 24 (termination/early discontinuation). In case of the 6 months extended study, the last MSFC was performed at months 30 (termination/early discontinuation of the extended study).
12. Subject-reported fatigue was assessed by the Modified Fatigue Impact Scale (MFIS) at months 0, 6, 12, 18, and 24 (termination/early discontinuation). In case of the 6 months extended study, additional MFIS was performed at month 30 (termination/early discontinuation of the extended study).
13. The general health status was assessed by the EuroQoL (EQ5D) questionnaire at month 0 (baseline) and month 24 (termination/early discontinuation of the study). In case of the 6 months extended study, the last EuroQoL (EQ5D) was performed at month 30 (termination/early discontinuation of the extended study) instead of month 24.
14. The general health status was assessed by the Short-Form general health survey (SF-36) subject-reported questionnaire at month 0 (baseline) and every 6 months thereafter, until termination/early discontinuation.
15. The subject underwent 5 assessments of binocular low-contrast visual acuity using the 100%, 2.5% and 1.25% contrast level charts [Sloan letter or Tumbling-E] in each assessment, at months 0 (baseline), 6, 12, 18 and 24 (termination/early discontinuation). In case of extending the study for 6 months, additional binocular low-contrast visual acuity assessment is performed at month 30 (termination/early discontinuation of the extended study).
16. Serum samples were collected from all subjects in order to investigate the potential mechanism of action of laquinimod and additional biomarkers of inflammation and potential biomarkers of MS disease at months: 0, 1, 12 and 24. In case of extending the study for 6 months the last serum sample is performed at month 30 (termination/early discontinuation of the extended study) instead of month 24.
17. The subjects underwent 3 MRI scans at months 0 (baseline), 12 and 24 (termination/early discontinuation). In case of the 6 months extended study, an additional MRI was performed at month 30 (termination/early discontinuation of the extended study).

18. Population PK study (PPK): Blood samples for PPK evaluation were collected from all subjects at months 1, 12 and 24. In case of extending the study for 6 months the last PPK evaluation was performed at month 30 (termination/early discontinuation of the extended study) instead of month 24.
19. Relapses were confirmed/monitored through the study. Since the "in study" relapse definition must be supported by an objective neurological evaluation, a neurological deficit must sustain long enough to eliminate pseudo-relapses. Therefore, in this clinical trial, a relapse was the appearance of one or more new neurological abnormalities or the reappearance of one or more previously observed neurological abnormalities wherein the change in clinical state lasts at least 48 hours and is immediately preceded by an improving neurological state of at least thirty (30) days from onset of previous relapse.
20. The allowed treatment for a relapse was intravenous Methylprednisolone 1 gr/day for up to 5 consecutive days.

Baseline Disease Characteristics of Patients is shown in Table 1 below:

Re-Consent Criteria

Upon a confirmed diagnosis of MS relapse, (as defined in the protocol) or an increase in EDSS in ≤2.0 points, sustained for ≥3 months, the following actions were taken:
1. The subject was reminded of the current available MS medications and the opportunity to terminate the study as written in the informed consent form.
2. The subject was requested to re-sign an informed consent form if he/she chooses to continue to participate in the study, in the same treatment assignment.

Safety stopping rules were set in place for the management of: 1) elevated liver enzymes, 2) inflammatory events, 3) thrombotic events and 4) pancreatitis.

Ancillary Studies:
1. Frequent MRI (selected countries and sites only): The cumulative number of $T_1$-Gd enhancing lesions taken from scans obtained at months 0, 3, 6, 12, and 24, and in case the study is be extended, 30. Additional MRIs for the ancillary study are performed at months 3 and 6.
2. Magnetization Transfer (MT) (selected countries and sites only): the change from baseline to month 12 and 24/30

TABLE 1

| Characteristic | Laquinimod 0.6 mg daily (n = 550) | Placebo (n = 556) | All (N = 1106) |
|---|---|---|---|
| Relapses in last year prior to screening | | | |
| Mean (SD) | 1.2 (0.7) | 1.3 (0.7) | 1.2 (0.7) |
| Median | 1.0 | 1.0 | 1.0 |
| Range | 0.0 to 4.0 | 0.0 to 5.0 | 0.0 to 5.0 |
| Relapses in last 2 years prior to screening | | | |
| Mean (SD) | 1.9 (1.0) | 1.9 (1.0) | 1.9 (1.0) |
| Median | 2.0 | 2.0 | 2.0 |
| Range | 0.0 to 7.0 | 0.0 to 7.0 | 0.0 to 7.0 |
| EDSS | | | |
| Mean (SD) | 2.6 (1.3) | 2.6 (1.3) | 2.6 (1.3) |
| Median | 2.5 | 2.5 | 2.5 |
| Range | 0.0-5.5 | 0.0-6.0 | 0.0 to 6.0 |
| Time from first symptom (years) | | | |
| Mean (SD) | 8.7 (6.9) | 8.7 (6.7) | 8.6 (6.8) |
| Median | 7.0 | 7.0 | 7.0 |
| Range | 0.5 to 34.5 | 0.4 to 32.8 | 0.4 to 34.5 |
| History of disease-modifying treatment | 206 | 212 | 418 |
| Number (%) | 210 (38.2%) | 221 (39.7%) | 431 (38.9%) |
| Interferon beta-1a | 132 | 123 | |
| Interferon beta-1b | 76 | 82 | |
| Interferon | 4 | 3 | |
| Glatiramer acetate | 84 | 89 | |
| Number of T1 GdE lesions | | | |
| Mean (SD) | 1.7 (3.9) | 2.0 (5.7) | 1.9 (4.9) |
| Median | 0.0 | 0.0 | 0.0 |
| Range | 0.0-30.0 | 0.0-84.0 | 0.0-84.0 |
| T2 lesion volume, mm³ | | | |
| Geometric mean (CV %) | 7.27 (46.1) | 7.31 (44.8) | 7.29 (45.5) |
| Median | 6.3 | 6.8 | |
| Range | 0.0 to 82.1 | 0.0 to 77.5 | |
| Normalized brain volume, cm³ | | | |
| Mean (SD) | 1578.9 (94.3) | 1584.7 (92.1) | 1581.3 (93.2) |
| Median | 1578.0 | 1590 | 1583.0 |
| Range | 1312.0 to 1823.0 | 1299.0 to 1824.0 | 1299.0 to 1824.0 | months in magnetization transfer MRI. MT was assessed at months 0 (baseline), 12 and 24 (termination/early discontinuation). In case of the 6 months extended study, the last MT was performed at month 30 (termination/early discontinuation of the extended study) instead of month 24.

3. Magnetization Resonance Spectroscopy (MRS) (selected countries and sites only): Change from baseline to 24/30 in Magnetic Resonance Spectroscopy (NAAS: Cr ratio in lesions, normally-appearing white matter). MRS was assessed at months 0 (baseline), and 24 (termination/early discontinuation). In case of the 6 months extended study, the last MRS was performed at month 30 (termination/early discontinuation of the extended study) instead of month 24.

4. Pharmacogenetic (PGx) assessment: Blood samples for PGx parameters were collected from all subjects at screening.

5. Brain atrophy, as defined by the percentage of change from one scan to the subsequent scan in brain volume, in addition to the measurements done in the main study (Frequent MRI Cohort).

6. Whole blood and serum samples (selected countries and sites only) were collected for evaluation of the immunological response to treatment with laquinimod and further investigation of the potential mechanism of action. Whole blood samples were collected at months: 0, 1, 3, 6, 12 and 24. Serum samples were collected at month: 0, 1, 6, 12 and 24 (even if the study is extended to month 30).

7. Relationship between PGx and response to laquinimod in terms of clinical, MRI and safety parameters.

Inclusion/Exclusion Criteria

Inclusion Criteria

1. Subjects must have a confirmed and documented diagnosis as defined by the Revised McDonald Criteria (Polman, 2005), with relapsing-remitting disease course.
2. Subjects must be ambulatory with converted Kurtzke EDSS score of 0-5.5.
3. Subjects must be in a stable neurological condition and free of corticosteroid treatment [intravenous (iv), intramuscular (im) and/or per os (po)] 30 days prior to screening (month −1).
4. Subjects must have experienced one of the following:
   a. At least one documented relapse in the 12 months prior to screening.
   b. At least two documented relapses in the 24 months prior to screening.
   c. One documented relapse between 12 and 24 months prior to screening with at least one documented T1-Gd enhancing lesion in an MRI performed within 12 months prior to screening.
5. Subjects must be between 18 and 55 years of age, inclusive.
6. Subjects must have disease duration of at least 6 months (from the first symptom) prior to screening.
7. Women of child-bearing potential must practice an acceptable method of birth control. Acceptable method of birth control in this study include: surgical sterilization, intrauterine devices, oral contraceptive, contraceptive patch, long-acting injectable contraceptive, partner's vasectomy or double barrier method (condom or diaphragm with spermicide).
8. Subjects must be able to sign and date a written informed consent prior to entering the study.
9. Subjects must be willing and able to comply with the protocol requirements for the duration of the study.

Exclusion Criteria

1. Subjects with progressive forms of MS.
2. An onset of relapse, unstable neurological condition or any treatment with corticosteroids [(iv), intramuscular (im) and/or per os (po)] or ACTH between months −1 (screening) and 0 (baseline).
3. Use of experimental or investigational drugs, and/or participation in drug clinical studies within the 6 months prior to screening.
4. Use of immunosuppressive including mitoxantrone (Novantrone®) or cytotoxic agents within 6 months prior to screening visit.
5. Previous use of any one of the following: natalizumab (Tysabri®), caldribine, laquinimod.
6. Previous treatment with glatiramer acetate (Copaxone®) Interferon-β (either 1a or 1b) or intravenous immunoglobulin (IVIG) within 2 months prior to screening visit.
7. Systemic corticosteroid treatment of ≥30 consecutive days duration within 2 months prior to screening visit.
8. Previous total body irradiation or total lymphoid irradiation.
9. Previous stem cell treatment, autologous bone marrow transplantation or allogenic bone marrow transplantation.
10. A known history of tuberculosis.
11. Acute infection two weeks prior to baseline visit.
12. Major trauma or surgery two weeks prior to baseline.
13. Use of inhibitors of CYP3A4 within 2 weeks prior to baseline visit (1 month for fluoxetine).
14. Use of amiodarone within 2 years prior to screening visit.
15. Pregnancy or breastfeeding.
16. A ≥3×ULN serum elevation of either ALT or AST at screening.
17. Serum direct bilirubin which is 2×ULN at screening.
18. A QTc interval which is 450 msec (according to machine output) obtained from:
    a. Two ECG recordings at screening visit, or
    b. The mean value calculated from 3 baseline ECG recordings.
19. Subjects with clinically significant or unstable medical or surgical condition that would preclude safe and complete study participation, as determined by medical history, physical examination, ECG, laboratory tests or chest X-ray. Such conditions may include:
    a. A cardiovascular or pulmonary disorder that cannot be well-controlled by standard treatment permitted by the study protocol.
    b. A gastrointestinal disorder that may affect the absorption of study medication.
    c. Renal or metabolic diseases.
    d. Any form of chronic liver disease.
    e. Known human immunodeficiency virus (HIV positive status.
    f. A family history of Long-QT syndrome.
    g. A history of drug and/or alcohol abuse.
    h. Major psychiatric disorder.
20. A known history of sensitivity to Gd.
21. Inability to successfully undergo MRI scanning.
22. Known drug hypersensitivity that would preclude administration of laquinimod, such as hypersensitivity to: mannitol, meglumine or sodium stearyl fumarate.

Outcome Measures

Neurological evaluations, including safety assessments, were performed at screening, baseline and every three months up to month 24. Patient neurological assessments and general medical evaluations were conducted by two neurologists in order to minimize the possibility of unblinding; a specially trained and certified examining neurologist assessed neurological condition, and the treating neurologist determined whether a subject had experienced a relapse based on EDSS/Functional Systems scores.

The primary endpoint was the number of confirmed relapses during the double-blind study period. A relapse was defined as the appearance of one or more new neurological abnormalities or the reappearance of one or more previously observed neurological abnormalities lasting for at least 48 hours and after an improved neurological state for at least 30 days. An event was counted as a relapse if the subject's symptoms were accompanied by observed objective neurological changes consistent with at least one of the following: an increase of at least 0.5 in the EDSS score; an increase of one grade in two or more of the seven functional systems; or an increase of two grades in one functional system. Standardized treatment of relapses was intravenous methylprednisolone 1 g/day for up to five consecutive days based on the treating neurologist's decision.

Secondary endpoints were disability progression as measured by the EDSS and the Multiple Sclerosis Functional Composite (MSFC). Confirmed disability progression was defined as an increase of ≥1.0 EDSS point from baseline if baseline EDSS was between 0 and 5.0, or an increase of ≥0.5 point if baseline EDSS was ≥5.5. In order to confirm EDSS progression, these increases had to be sustained for at least three months. Additional predefined disability endpoints include the proportion of patients without confirmed disability progression at 24 months; confirmed disability progression (defined as change in EDSS scores ≥1.0 points for baseline EDSS 0 to 5.0 or ≥5.5) sustained for six months; the accumulation of physical disability as measured by mean EDSS and the mean change in EDSS from baseline to last observed value (LOV).

For the MSFC, the measure was the total MSFC z score at 24 months (including patients who terminated after 12 months). The 9-hole peg test (9HPT) and the Paced Auditory Serial Addition Test (PASAT) were performed three times at screening to reduce confounding training effects during the trial.

MRI related secondary endpoints were the cumulative number of GdE lesions at months 12 and 24; and the cumulative number of new T2 lesions (relative to previous scan) at months 12 and 24; MRI exploratory endpoints included percent change of brain volume using SIENA.

Additional MRI methodological details are as follows: In all patients, MRI scans were performed at 0, 12, and 24 months. Before a site could enroll study participants they were required to image a volunteer patient with definite MS twice with repositioning according to a strict study imaging protocol using scanners with a minimum field strength of 1.5 T. Fast/turbo spin echo (repetition time [TR]=2200-3500 ms, echo time [TE]=14-50/90-120 ms, echo train length=2-7, slice thickness=3 mm, and contiguous axial slices=44) sequences were used to obtain proton density and T2-weighted images. High resolution pre-contrast 3D T1-weighted sequences (TR=8-15 ms, TE=3-5 ms, inversion time=1.1 s, number of slices 160, slice thickness 1.2 mm, flip angle [FA]=10-15, orientation sagittal) were acquired for quantification of brain atrophy. Finally, T1-weighted images (1.5 T scanners: conventional spin echo sequence; TR=600-650 ms, TE=10-20 ms, slice thickness=3 mm, and contiguous axial slices=44; 3.0 T scanners: 3D sequence; TR=5-9 ms, TE=2-5 ms, FA=15, slice thickness=3 mm, and contiguous axial slices=44) were obtained 5 minutes after injection of 0.1 mmol/kg of gadolinium. A series of axial, coronal, and sagittal images was obtained to create an axial reference scan for subsequent careful repositioning of each patient at the follow-up session. Axial slices were positioned to run parallel to a line joining the most inferioanterior and inferioposterior parts of the corpus callosum.

Image quality was reviewed at the MRI-AC using predetermined criteria. The identification of GdE and T2-hyperintense lesions was done by consensus of two experienced observers. The number of total and new GdE lesions and new/enlarging T2-hyperintense lesions were counted. The identified lesions were then outlined by trained technicians using a semiautomated segmentation technique based on local thresholding (Jim 4.0; Xinapse System, Leicester, UK) and lesion volumes were calculated automatically. Percentage brain volume changes and cross-sectional normalized brain volumes were measured on postcontrast T1-weighted images, with Structural Image Evaluation of Normalized Atrophy (SIENA) software and a cross-sectional method (SIENAX) (available from the FMRIB Software Library, Oxford University, Oxford, UK; http://www.fmrib.ox.ac.uk/analysis/research/siena/siena).

Primary Outcome Measure

The number of confirmed relapses (and Annualized relapse rate) during the double blind study period.

Secondary Outcome Measures
1. Accumulation of physical disability measured by the time to confirmed progression of EDSS during the study period (A confirmed progression of EDSS is defined as a 1 point increase from baseline on EDSS score if baseline EDSS was between 0 and 5.0, or a 0.5 point increase if the baseline EDSS was 5.5, confirmed 3 months later. Progression cannot be confirmed during a relapse).
2. Disability, as assessed by the MSFC score at the end of the treatment period (month 24/30).
3. The cumulative number of new T2 lesions on scans taken on months 12 and 24 (and 30 in the case of the 6 months extended study).
4. The cumulative number of enhancing lesions on T1-weighted images taken on months 12 and 24 (and 30 in case of extending the study for 6 months.)

Safety and Tolerability Outcome Measures
1. Adverse events.
2. Vital signs.
3. Weight.
4. Physical examination.
5. Electrocardiogram (ECG) findings.
6. Clinical laboratory parameters.
7. Proportion of subjects (%) who prematurely discontinued from the study, reason of discontinuation and the time to withdrawal.
8. Proportion of subjects (%) who prematurely discontinued form the study due to AEs and the time to withdrawal.

Additional Exploratory Endpoints

The following assessments are performed in an exploratory manner:
1. To assess the cumulative number of new hypointense lesions on enhanced $T_1$ scans at months 12 and 24 (and 30 in case of extending the study for 6 months).
2. Subject-reported fatigue as assessed by the Modified Fatigue Impact Scale (MFIS).
3. General health status by the EuroQoL (EQ5D) questionnaire.
4. The general health status assessed by the Short-Form general health survey (SF-36) subject-reported questionnaire.
5. The time to the first confirmed relapse during the study period.

6. The rate of confirmed relapses during the study period, requiring hospitalization and/or IV steroids.
7. The proportion of relapse free subjects.
8. The change in T2-lesion volume as defined by the change from baseline to month 12, from month 12 to month 24/30 and from baseline to month 24/30.
9. The change in $T_1$-hypointense lesion volume as defined by the change from baseline to month 12, from month 12 to month 24/30 and from baseline to month 24/30.
10. Brain atrophy as defined by the percentage of change from baseline to month 12, from month 12 to month 24/30 and from baseline to month 24/30 in brain volume.
11. Serum samples are collected from all subjects in order to investigate the potential mechanism of action of laquinimod and additional biomarkers of inflammation and potential biomarkers of MS disease. These samples are collected at months: 0 (baseline), 1, 12 and 24 (even if the study is extended to month 30).
12. Population PK—fitness of a population model to different covariates is evaluated. (covariates such as: gender, age, concomitant medications, weight, AE profile, habits).
13. The change from baseline to month 24/30 (termination/early discontinuation) in binocular visual acuity, as assessed by the number of letters read correctly from 2 meters distance on 100%, 2.5% and 1.25% contrast level Sloan letter/Tumbling-E charts.

Statistical Analysis

The analysis of the total number of confirmed relapses during the study period is based on baseline adjusted Quasi-Likelihood (over-dispersed) Poisson Regression. Using the Poisson regression with the treatment group as a covariate, the ARR of each group was calculated for the intent-to-treat (ITT) cohort as the total number of confirmed relapses for all patients in each group divided by the total patient years in that group. In addition to the treatment group, the following covariates were included: baseline EDSS score, log of the (prior 2-year number of relapses +1) and country or geographical region.

The analysis of the accumulation of physical disability is based on Cox's Proportional Hazard model. The analysis of MSFC is based on baseline-adjusted Analysis of Covariance. The analysis of the secondary MRI endpoints is based on baseline-adjusted Negative Binomial Regression. To control against type-I error, the secondary endpoints were analyzed only after a significant effect was found for the primary endpoint. Likewise, the study's overall type-I error was further controlled in the analysis of the secondary endpoints by applying the following gate-keeping approach: both the cumulative number of new/enlarging T2 and the cumulative number of GdE lesions at months 12 and 24 were tested simultaneously and needed to be statistically significant at $p<0.05$, or one needed to be significant at $p<0.025$ if the other endpoint was not statistically significant at the 5% level. If the above condition was met, the study then proceeded to the analysis of the confirmed EDSS progression endpoint, if this endpoint was significant at 5% level, the analysis was done for the total MSFC z-scores.

Sample size calculations were based on assumptions that the number of confirmed relapses in one year reflects an over-dispersed Poisson distribution, and that the expected ARR was 0.65 in untreated subjects, 0.6 in the placebo group due to a placebo effect, and 0.45 in the laquinimod group based on 25% or more reduction in relapse rate compared to placebo. A simulation study showed that 830 subjects (415 subjects per arm) would provide approximately 90% power to detect a significant change in the ARR. To correct for anticipated 20% withdrawal over 24 months, the sample was adjusted to 1000 subjects (500 subjects per arm).

The analysis of risk to confirmed disability progression using the ITT cohort was based on Cox's Proportional Hazard model adjusted to baseline EDSS, log of the prior 2 year number of relapses +1 and geographical region. The MSFC at month 24 was analyzed using a baseline-adjusted ANCOVA (SAS@PROC GLM) with baseline MSFC as 1 degree of freedom covariate and baseline EDSS score, log of the 2-year prior relapse rate +1 and country or geographical region as additional covariates. Analyses of the MSFC z score at 24 months and the secondary MRI endpoints included only patients who did not discontinue from the trial prior to month 12 visit.

Analyses of the secondary MRI endpoints of the cumulative number of GdE and new/enlarging T2 lesions at 12 and 24 months involved a baseline-adjusted negative binomial regression with an "offset" employing the log of the relative exposure to adjust for early-terminated patients. The model included as covariates the number of enhancing lesions at baseline, and country or geographical region. In the case of new/enlarging T2 lesion analysis, the baseline T2 lesion volume was also added. The MRI secondary endpoints analyses were tested simultaneously with an overall type I error of 5%, using the Hochberg's step-up modification to Bonferroni's method to the two P-values obtained from the analyses of these two endpoints. The analysis of the brain atrophy endpoint involved a baseline-adjusted analysis of covariance (ANCOVA). The covariates were the number of GdE lesions at baseline and the country or region. The exploratory endpoints were all analyzed at a significance level of 5%.

Results

The results of the ALLEGRO trial indicated that laquinimod treatment effectively reduced annualized relapse rates, slowed the progression of disability, reduced brain atrophy, and reduced the development of new lesions. A summary of the study results is presented in Table 2 below:

TABLE 2

| | Laquinimod, 0.6 mg daily (n = 550) | Placebo (n = 556) | Effect |
|---|---|---|---|
| Relapses | | | |
| Annualized relapse rate[a] | | | 23% reduction |
| Adjusted means (SE) | 0.304 (0.022) | 0.394-0.395 (0.027) | |
| Risk ratio (95% CI) | 0.770 (0.650-0.911)) | | |
| Relapse-free during study[b] | | | 55% increase odds to be relapse free |
| Adjusted proportions | 62.90% | 52.24% | |
| Odds ratio (95% CI) | 1.550 (1.205-1.994) | | |
| Risk of first confirmed relapse[c] | | | |

TABLE 2-continued

|  | Laquinimod, 0.6 mg daily (n = 550) | Placebo (n = 556) | Effect |
|---|---|---|---|
| Hazard ratio (95% CI) | 0.718 |  |  |
| 95% Confidence Interval | 0.595-0.866 |  |  |
| Annualized rate of relapses requiring hospitalization and/or IV steroids[d] |  |  | 27% reduction |
| Adjusted Mean (SE) | 0.242 (0.020) | 0.334 (0.025) |  |
| Risk Ratio (95% CI) | 0.723 (0.606-0.862) |  |  |
| Time to 1st confirmed relapse |  |  | 28% reduction for the risk of 1st confirmed relapse |
| Disability |  |  |  |
| Risk for EDSS progression confirmed at 3 months[e] |  |  |  |
| Hazard Ratio (95% CI) | 0.641 (0.452-0.908) |  |  |
| Time to confirmed (3 Ms) progression - EDSS | 9.8% progressed | 14% progressed | 36% reduction of risk to progress |
| Patients with no confirmed disability progression (%) at LOV[f] | 496 (90.2%) | 478 (86.0%) |  |
| Risk for EDSS progression confirmed at 6 months[g] |  |  |  |
| Hazard Ratio (95% CI) | 0.516 (0.337-0.790) |  |  |
| Mean EDSS score at LOV (SE)[h] | 2.68 (0.046) | 2.790 (0.046) |  |
| 95% Confidence Interval | (2.59-2.77) | (2.70-2.88) |  |
| Median | 2.5 | 2.5 |  |
| Range | 0.0 to 8.0 | 0.0 to 8.5 |  |
| MSFC |  |  |  |
| Total z scores at 24 months (including early terminations after 12 months)[i] |  |  | 34% reduction of risk to progress |
| Mean (95% CI) | 0.056 (−0.000 to 0.112) | 0.0376 (−0.020 to 0.94) |  |
| MRI |  |  |  |
| Cumulative number of GdE lesions at months 12 and 24[j] |  |  | 37% reduction |
| No of patients with data | 479 | 464 |  |
| Mean (SE) | 1.332 (0.14) | 2.119 (0.22) |  |
| Median | 0.00 | 1.00 |  |
| Range | 0 to 49 | 0 to 91 |  |
| Risk ratio (95% CI) | 0.629 (0.488-0.809) |  |  |
| Cumulative number of new/enlarging T2 lesions at 12 and 24 months[k] |  |  | 30% reduction |
| No. of patients with data | 479 | 464 |  |
| Mean (SE) | 5.032 (0.079) | 7.148 (0.075) |  |
| Risk ratio (95% CI) | 0.704 (0.584-0.849) |  |  |
| Percent change of brain volume from baseline to month 24[l] |  |  | 32.8% reduction |
| No. of patients with data | 382 | 381 |  |
| Adjusted mean change at month 24 | −0.871 | −1.297 |  |
| Adjusted mean difference (95% CI) | 0.426 (0.267-0.585) |  |  |
| BA at month 12 | −0.358% | −0.763% | 53% reduction |
| T2 volume month 0 | 7.27 | 7.315 |  |
| T2 volume month 12 | 8.005 | 8.441 | 5% |
| T2 volume month 24 | 8.111 | 8.509 | 5% |
| BL to M 24 | 11.5% | 16% |  |
| Hypointense T1 volume month 0 | 2.65 | 2.65 |  |
| Hypointense T1 volume month 12 | 2.805 | 2.894 | ~1% |

TABLE 2-continued

|  | Laquinimod, 0.6 mg daily (n = 550) | Placebo (n = 556) | Effect |
|---|---|---|---|
| Hypointense T1 volume month 24 | 2.829 | 2.891 | ~1% |
| BL to M 24 | 7% | 9% | |
| Cumulative new Hypointense T1 months 12 + 24 | 1.468 | 2.002 | 27% reduction |

[a] Baseline adjusted Quasi-likelihood (over-dispersed) Poisson Regression analysis, including baseline EDSS score, log of the prior 2-year relapse rate + 1 and country or geographical region as covariates.
[b] Baseline adjusted logistic regression analysis with covariates baseline EDSS, log of the prior 2-year number of relapse + 1 and country or geographical region.
[c] Cox model regression analysis adjusted to baseline EDSS, log of the prior 2-year number of relapses + 1 and geographical region.
[d] Baseline adjusted Quasi-likelihood (over-dispersed) Poisson Regression analysis, including baseline EDSS score, log of the prior 2-year relapse rate + 1 and country or geographical region as covariates.
[e] Cox Model regression analysis adjusted to baseline EDSS, log of the prior 2-year number of relapses + 1 and geographical region.
[f] The p-value was calculated using the chi square test.
[g] Cox Model regression analysis adjusted to baseline EDSS, log of the prior 2-year number of relapses + 1 and geographical region.
[h] Baseline adjusted ANCOVA with geographical region, EDSS at baseline and the log of the prior 2-year relapse rate + 1 as covariates.
[i] Baseline adjusted ANCOVA with baseline MSFC as 1 degree of freedom covariate and baseline EDSS score, log of the prior 2-year relapse + 1 and country or geographical region as covariates.
[j] Baseline-adjusted Negative Binomial Regression with an offset to adjust for early termination lack of exposure and baseline GdE lesions, and country or geographical region as covariates.
[k] Baseline-adjusted Negative Binomial Regression with an offset to adjust for early termination lack of exposure and baseline GdE lesions, and country or geographical region as covariates.
[l] Baseline-adjusted ANCOVA with the number of baseline GdE lesions, and country or geographical region as covariates.

A summary of a post-hoc study results is presented in Table 3 below:

TABLE 3

|  | Placebo | Laquinimod | Effect |
|---|---|---|---|
| ARR 1st year | 0.452 | 0.343 | 24% reduction |
| No recovery | 0.08 | 0.06 | 24% reduction |
| Full recovery | 0.179 | 0.155 | 13% reduction |
| ARR for dropouts | 0.872 | 0.640 | 26% reduction |
| Unconfirmed relapses | 0.112 | 0.094 | 17% reduction |
| Relapses requiring hospitalization | 0.114 | 0.071 | 38% reduction |
| Relapses requiring IV steroids | 0.359 | 0.263 | 27% reduction |
| ARR by median relapse duration: | | | |
| ≤34 days | 0.243 | 0.153 | 37% reduction |
| >34 days (n ~100) | 0.976 | 0.964 | 1.3% reduction |
| New-T1 Hypointense Lesions | | | |
| M 12 | 1.461 | 1.074 | 27% reduction |
| M 24 | 1.806 | 1.230 | 32% reduction |
| T1 Hypointense Lesion free | | | |
| M 12 | 50.2% | 56.3% | 28% odds |
| M 24 | 43.1% | 52.8% | 47% odds |
| BA from M 12 to M 24 | −0.561 | −0.548 | |
| BA for pts with all scans: | | | |
| Change BL to M 12 | −0.746 | −0.337 | 60% |
| to M 24 | −1.268 | −0.855 | 57% |
| % BVC BL to M 24 | | | |
| MRI free YES | −1.078 | −0.533 | 45.5% |
| NO | −1.346 | −1.001 | 65.5% |
| GdE counts M 12 | 1.142 | 0.731 | 36% reduction |
| M 24 | 0.793 | 0.482 | 39% reduction |
| GdE lesion free M 12 | 59.9% | 69% | 49% odds |
| M 24 | 62.8% | 74.5% | 72% odds |
| GdE volume M 12 | 1.109 | 1.058 | 4.5% |
| M 24 | 1.091 | 1.045 | 4.7% |
| T2 lesion free M 12 | 24.2% | 30.8% | 39% odds |
| M 24 | 15.4% | 20.3% | 40% odds |
| New T2 lesion #M 12 | 4.23 | 2.81 | 33.5% |
| M 24 | 6.50 | 4.45 | 31.5% |

TABLE 3-continued

|  | Placebo | Laquinimod | Effect |
|---|---|---|---|
| % BV change M 24 | | | |
| GdE = 0 | −1.218 | −0.859 | 30% reduction |
| GdE > 0 | −1.380 | −0.881 | 37% reduction |
| Cum # T1 GdE by previous medications: | | | |
| naïve | 1.937 | 1.135 | 42% reduction |
| not naive | 2.562 | 1.746 | 32% reduction |
| Cum New T2 by previous medications: | | | |
| naïve | 7.403 | 4.967 | 33% reduction |
| not naive | 6.661 | 5.075 | 24% reduction |
| T1 hypointense by previous medications: | | | |
| naïve | 2.189 | 1.585 | 28% reduction |
| not naive | 1.627 | 1.217 | 25% reduction |
| % BV change by previous medications: | | | |
| naïve | −1.327 | −0.82 | 38% reduction |
| not naive | −1.241 | −0.954 | 23% reduction |
| Time to confirmed (3 Ms) progression - EDSS | 14% progressed | 9.8% progressed | 36% reduction of risk to progress |
| MSFC at M 24 | 0.037 | 0.056 | 34% reduction of risk to progress |

* Recover refers to EDSS before and after attack

Oral Laquinimod Reduced Severe Relapses and Slowed Disability Progression

Relapse Endpoints:

The ARR during the 24-month treatment period was significantly reduced in the laquinimod patients compared to placebo patients (0.304±0.022 vs 0.395±0.027, p=0.0024, Table 2). This result was robust and consistent in all analysis sets. Other relapse-related measures, such as time to first relapse and relapse free rates were also positively changed following laquinimod treatment as compared to placebo. The percentage of relapse-free patients was 62.9% for laquinimod and 52.24% for placebo subjects (p=0.0006, Table 2), corresponding to an increase of 55% in the odds to be relapse-free. The time to the first relapse was prolonged for laquinimod patients compared to placebo participants (increase of 28.2% in the time to first relapse, p=0.0005) and the risk for relapse was significantly reduced. The annualized rate of relapses requiring hospitalizations and/or intravenous steroid treatment, an exploratory endpoint of the study, was found to be significantly lower for patients treated with laquinimod compared with those in the placebo arm (p=0.0003). The annualized rate of relapses requiring IV steroids was 27% lower for laquinimod patients (0.263 vs 0.359, p<0.0001). The annualized rate of relapses requiring hospitalization was 0.071 vs. 0.114, p<0.0001, a 38% reduction for laquinimod patients. Based on the reduction in relapse rate, it can be said that laquinimod reduces the likelihood that a relapsing-remitting multiple sclerosis human patient would experience a confirmed relapse within a predetermined time period.

Disability Endpoints:

The ALLEGRO results clearly show that laquinimod reduced both relapse severity and accumulation of disability in patients with RRMS.

In this study, secondary endpoint on disability included the risk to disability progression (change in EDSS score ≥1.0 points if baseline EDSS 0-5.0 or change ≥0.5 point if baseline EDSS≥5.5) confirmed at 3 months. Predefined additional disability endpoints included the risk of disability progression confirmed at 6 months, the risk of disability progression at last observed value (LOV), and the proportion of patients with confirmed disability progression sustained for 3 months.

EDSS scores confirmed after 3 months was significantly decreased by 36% for laquinimod patients (hazard ratio=0.641, 95% CI: 0.452-0.908, p=0.0122; Table 2). There was also a 48% decrease in the risk for 6 month confirmed EDSS progression (HR=0.516, 95% CI: 0.337-0.790, p=0.0023). This observation was reinforced by the 35% reduction in risk of confirmed progression using the more stringent approach requiring the persistence of EDSS change at the last available visit (hazard ratio=0.656, p=0.036). The proportion of patients with confirmed EDSS progression after 24 months was 9.8% for laquinimod and 14.0% for placebo (p=0.038; Table 2). A post-hoc subgroup analysis indicated that 33/54 (61.1%) laquinimod and 53/78 (67.9%) placebo patients who progressed also had a relapse during the study. There was little overall change in the MSFC scores from baseline to month 24 and no significant differences were found between the adjusted mean total MSFC z scores for laquinimod and placebo treated patients at 24 months (z scores=0.056 and 0.037, respectively, p=0.5893). The significant decrease in time to and risk for confirmed progression disease activity, as measured by, e.g., the EDSS score of the patient, is suggestive of laquinimod having a neuroprotective property.

This clinical finding was supported by MRI measures (defined as exploratory endpoints), such as progression of brain atrophy and T1-hypointense lesion counts. The MRI results are discussed in more detail below.

Oral Laquinimod Reduced MRI Markers of Neurodegeneration

Secondary endpoints of the ALLEGRO trial included disease activity as measured by MRI, including counts of Gadolinium enhancing T1 lesions and new-T2 hyperintense lesions. The study evaluated laquinimod's effects on a variety of conventional (T1 hypointensity and brain volume) and advanced (magnetization transfer (MT) imaging and proton magnetic resonance spectroscopy ($^1$H-MRS)) MRI measures of tissue damage. Conventional MRI scans for new T1 hypointense lesions, and brain volume using SIENA were performed at baseline, 12 and 24 months. At 10 sites (n=93), MT MRI was obtained at the three time points and at 6 sites (n=39), NAA/Cr ratios from $^1$H-MRS were obtained from a volume of interest (VOI) placed in the central white matter at baseline and last study visit.

Laquinimod was found to reduce the mean cumulative number of GdE lesions compared to placebo by 37% (risk ratio=0.629, p=0.0003). The mean cumulative number of new/enlarged T2 lesions at months 12 and 24 was also reduced in laquinimod patients by 30% (risk ratio=0.704, p=0.0002). The mean cumulative number (at month 12 and 24-termination/early termination after month 12) of new hypointense T1 lesions was reduced by 26.7% in the laquinimod group compared to placebo group (1.47 vs 2.00 respectively, p=0.0039). Change in mean MTR whole brain from baseline to last observed value (LOV) decreased for placebo patients (n=40) by −0.438 and on the contrary remained stable for laquinimod patients (+0.045 change, n=44), representing a difference of 0.483 (p=0.0180). In the same direction, the average MTR of T2 visible lesions was decreased by −0.335 for placebo patients (n=40) and stable for laquinimod patients (−0.005 change, n=43), representing a difference of 0.330 (p=0.1007). The adjusted mean change in NAA/Cr from baseline to month 24 was 0.087 for laquinimod (n=12) and −0.145 for placebo (n=15) patients (p=0.1738).

The percent change in brain volume progressed at a greater rate in the placebo group compared to the laquinimod group from baseline to 12 months, −0.763 vs. −0.358 and from baseline to 24 months −1.297 vs −0.871, (adjusted mean difference=0.426, p<0.0001) respectively, reflecting a 51.7% and 32.8% reduction in brain atrophy by laquinimod treatment.

The MRI data show that laquinimod had a clear effect in preventing irreversible tissue loss and is consistent with its impact on disability progression.

Laquinimod Maintained or Improved Fatigue and Functional Status of Patients

As patient-reported exploratory endpoints, fatigue was assessed using the Modified Fatigue Impact Scale (MFIS) and functional status using the short-form (SF)-36 general health survey. Both measures were completed at the baseline, 6, 12, 18 and 24 month clinic visits and were analyzed using an ANCOVA adjusted for baseline EDSS, 2-year prior relapse rate and country/region. A summary of the quality of life (QOL) results is presented in Table 4 below:

TABLE 4

| Exploratory | Placebo | Laquinimod | Effect | p |
|---|---|---|---|---|
| MFIS | 34.4 | 31.9 | −2.53 | 0.004 |
| Subject-Reported Fatigue -the Modified Fatigue Impact Scale | | | | |
| While the mean total MFIS score for those treated with laquinimod 0.6 mg at Month 24 remained stable, the mean total MFIS score for those treated with placebo had increased reflecting increased functional disability due to fatigue. From the patients' perspectives, laquinimod 0.6 mg was, on average, associated with less functional disability due to fatigue than placebo at Month 24 | | | | |
| SF36 - SFMHD | −2.314 | −0.47 | 1.848 | 0.001 |
| Mental component summary | | | | |
| The MCS score at Month 24 for those treated with laquinimod 0.6 mg remained stable while the MCS score for those treated with placebo declined. The patients' self-assessment of their mental health status with laquinimod 0.6 mg was, on average, better than with placebo at Month 24 | | | | |
| SF36 - SFPHD | −1.169 | −0.519 | 0.65 | 0.1354 |
| Physical component summary | | | | |
| The PCS score at Month 24 for those treated with laquinimod 0.6 mg remained stable while the PCS score for those treated with placebo declined. The patients' self-assessment of their mental health status with laquinimod 0.6 mg was, on average, better than with placebo at Month 24 | | | | |
| EQ5D | 68.6 | 71.0 | −2.366 | 0.0267 |
| General Health Status by the Euroqol Questionnaire was assessed with the 5 dimension EQ-5D descriptive profile (Mobility, Self Care, Usual Activities, Pain or Discomfort, and Anxiety or Depression) The results of the individual EQ-5D dimensions analyses show that those treated with laquinimod 0.6 mg maintained their health status at Month 24 while those treated with placebo reported a decline, on average, in health status. Dimensions with the most variation in health status between treatments at Month 24 were Mobility, Self-Care, and Anxiety or Depression | | | | |
| Mobility | | | 1.497 | 0.0181 |
| Self care | | | 2.251 | 0.0337 |
| Usual activities | | | 1.129 | 0.4051 |
| Pain discomfort | | | 1.036 | 0.8024 |
| Anxiety or Depression | | | 1.425 | 0.0113 |

At baseline fatigue was more than twice the published mean scores for healthy individuals: 31.1 (0.79) for laquinimod and 30.6 (0.73) for placebo patients. Fatigue worsened in placebo patients during the trial with an adjusted mean score at 24 months of 34.4 (0.71) compared to those treated with laquinimod of 31.9 (0.71), a treatment effect for laquinimod of −2.53, (p=0.004). Changes in adjusted mean MFIS subscale scores from baseline showed a significant improvement in the laquinimod group: cognitive at 24 months (p=0.05); physical at 24 months (p=0.02); and psychosocial at 12 months (p=0.02). For the SF-36, the adjusted treatment effect difference between laquinimod and placebo on the mental component summary was 1.68 (p=0.004), with the subscales for vitality, social functioning and role emotional contributing to this effect. Although the physical component summary (PCS) remained stable for laquinimod over 24 months and the PCS for the placebo group declined, the difference did not reach statistical significance (p=0.13). Two of the PCS subscales: physical functioning (p=0.016) and role physical (p=0.010) showed improvement over 24 months with laquinimod versus placebo.

The results of the ALLEGRO trial suggest that fatigue and functional status of patients treated with laquinimod was maintained or improved compared to that of placebo patients and that these effects support the robust clinical effects seen on disability progression and relapse rate.

Safety and Tolerability

No deaths occurred in the laquinimod group and 3 deaths occurred in the placebo group (injury, suicide and complications related to pneumonia). A total of 122 serious adverse events (SAEs) were reported for laquinimod and 90 for placebo patients. A higher incidence of appendicitis was reported in laquinimod treated patients (5 cases versus 1 in the placebo group). In all cases appendectomy was performed without additional complications and patients continued with study treatment. Overall, there were 14 cases of neoplasms evenly distributed across both arms (8 in laquinimod and 6 in placebo groups) with a large variability in the type of cancers.

There were 3309 and 2965 adverse events in the laquinimod and placebo arms with 87% and 81% of patients reporting 1 or more events, respectively. The 3 most common adverse events in the laquinimod group compared to placebo (excluding liver enzyme elevations discussed below) were abdominal pain (n=32, 5.8% vs. n=16, 2.9%), back pain (n=90, 16.4% vs. n=50, 9%) and cough (n=41, 7.5% vs n=25, 4.5%). These adverse events were rarely associated with study discontinuation, (3% of laquinimod and 1% of placebo patients). More laquinimod patients (n=27, 4.9%; vs n=11, 2.0% in placebo) showed a shift to abnormal values in the liver aminotransferases, specifically, alanine aminotransferase (ALT) ≥3 times upper limit normal (3×ULN) and <5×ULN during the study. Treatment discontinuation occurred in 7 laquinimod and 2 placebo patients due to ALT≥3 and <5×ULN. By contrast, ALT elevations ≥5×ULN occurred equally often in both groups (8 vs. 8) and led to equal rates of discontinuation. Elevations up to 5×ULN usually occurred within the first 6 months and all were reversible either without study discontinuation or within 2 months of withdrawal. There were no cases of liver failure and no cases of liver insufficiency as evidenced by concomitant elevations of bilirubin or coagulation tests (Hy's Law) (Temple, 2006).

Discussion

Laquinimod is a promising a treatment for relapsing remitting MS, based on its effects on the accumulation of tissue damage, as indicated by consistent effects on clinical measures of disability and MRI measures of disease burden, its oral route of administration and its safety profile.

Laquinimod had a significant effect on inflammatory activity which characterizes the relapsing remitting course of MS. The effect was seen in the reduction of relapse rate, the primary end point of the study, as well as reduction of active MRI lesions. The reduction of relapse rate was highly consistent with effects seen on MRI measures of disease activity, which has not always been the case for other disease modifying treatments (DMTs) (The IFNB Multiple Sclerosis Study Group, 1993; Jacobs, 1996; PRISMS Study Group, 1998). Moreover, laquinimod had a significant effect on confirmed disability progression, which is considered a core outcome measure in MS. Although the overall proportion of patients with disease progression in the placebo arm was modest, the reduction in the laquinimod arm was a real phenomenon, as the effect was confirmed by sensitivity analyses including the more stringent criteria of disability progression, such as the 6 month confirmation period and the persistence of the EDSS change at the last available visit. Subgroup analyses showed that disability progression in both groups was predominantly due to attacks, which were less severe and followed by a better recovery in laquinimod treated patients. This is in line with preclinical studies which show a moderate effect of the drug on lesion numbers and a pronounced effect on the axonal damage inside the lesions (Thöne, 2011). The peculiar property of laquinimod to reduce the accumulation of irreversible tissue damage in MS is further supported by the significant decrease in the progression of brain tissue loss which was similar in magnitude to what has been reported previously for other DMTs (Kappos, 2010; Rudick, 1999; Sormani, 2004; Miller, 2007) that have a larger impact on inflammatory activity. No significant effects were observed for MSFC, likely due to the very small mean longitudinal changes seen in both arms. A practice effect may have obscured longitudinal changes of the MSFC components as there was an improvement of the MSFC scores in the placebo arm, whereas other trials have shown a deterioration (Kappos, 2010; Cohen, 2010).

The ALLEGRO study further confirmed the very good safety profile of laquinimod demonstrated in phase II. There were no increased rates of serious adverse events in the trial. One safety signal was liver enzyme elevations which occurred two times more frequently in the laquinimod treated arm. These elevations occurred mostly in the first treatment period and were usually modest; values exceeding 5×ULN occurred equally often in the laquinimod and placebo arms. The liver enzyme elevations were always reversible even in patients with ≥3×ULN and were never associated with clinical, imaging or laboratory signs of liver insufficiency or failure. One potential signal of a tolerability issue was abdominal pain which occurred more frequently and resulted in treatment discontinuation more frequently in the laquinimod arm. As with ALT elevations, abdominal pain was reported in the early phases of treatment exposure. It is worth noting that the safety concerns previously seen with roquinimex (Noseworthy, 2000) such as serositis, cardiovascular events and thrombosis did not emerge as signals in the ALLEGRO study.

The results seen in this study are unique. Data obtained from pivotal studies of other drugs with proven effect on progression of disability in a placebo-controlled setting, shows a magnitude of effect which is correlated with the effect on relapses. With all other drugs to date, the effect on progression of disability has been equal or lower than the effect on the ARR.

In comparison, the results of this study show that the effect of laquinimod on the progression of disability, which is a more important long-term measure of Multiple Sclerosis is considerably higher than other drugs, suggesting that the effect of laquinimod is not necessarily a derivative of its anti-inflammatory properties but also composed of pure neuroprotection, as seen in animal models. Therefore, this study shows that laquinimod is not only effective for treating MS by the way of its anti-inflammatory properties, it also provides neuroprotection to protect neural cells against neuronal injury or degeneration.

Conclusion

This phase III study supports laquinimod as a new option for the treatment of RRMS with reductions in relapses and disability progression and no safety signals other than a transient elevation of liver enzymes. No apparent increases was seen in infections or malignancies. Treatment with laquinimod was associated with reduction of annualized relapse rate from 0.395±0.027 for placebo patients to 0.304±0.022 for laquinimod patients (p=0.0024) and with a lower risk of confirmed EDSS progression (Hazard ratio=0.641, 95% CI: 0.452-0.908, p=0.0122). Mean cumulative number of GdE and new/enlarging T2 lesions were lower for laquinimod (p=0.0003 and p=0.0002), and the rate of brain volume reduction was reduced (p<0.0001) at month 24.

Example 2

Clinical Trial (Phase III)—Benefit-Risk Assessment of Avonex® and Laquinimod

A multinational, multicenter, randomized, parallel-group, clinical trial is performed in subjects with RRMS ("BRAVO"). BRAVO was conducted to assess the efficacy, safety and tolerability of laquinimod over placebo in a double-blinded and rater-blinded design and of a reference arm of Interferon β-1a (Avonex®). The study was also conducted to perform a comparative benefit/risk assessment between oral laquinimod and injectable Interferon β-1a (Avonex®).

The primary objective of the study was to assess the efficacy of 0.6 mg daily dose of laquinimod in subjects with RRMS as measured by the number of confirmed relapses during the treatment period. Secondary objectives of the study included assessing the effect of 0.6 mg daily dose of laquinimod on the accumulation of disability, as assessed by the MSFC score at the end of the treatment period; assessing the effect of 0.6 mg daily dose of laquinimod on the development of brain atrophy as defined by the percent brain volume change from baseline at the end of the treatment period; and assessing the effect of 0.6 mg daily dose of laquinimod on the accumulation of physical disability as measured by the time to confirmed progression of EDSS during the treatment period.

The 2006 EMEA Guidelines for MS clinical trials states that active control parallel group trials comparing the new treatment to an already approved treatment are needed in order to give the comparative benefit/risk ratio of the new treatment, at least in those treatment intended to prevent relapses. Three-arm studies with placebo, test product and active control are a preferred design.

Avonex® (Interferon beta-1a) is a 166-amino acid glycoprotein produced by recombinant DNA technology using genetically engineered Chinese Hamster ovary cells into which the human interferon beta gene has been introduced. The amino acid sequence of Avonex® is identical to that of natural human interferon beta.

Avonex® is a marketed drug indicated for the treatment of patients with relapsing forms of MS to slow the accumulation of physical disability and decrease the frequency of clinical exacerbations. Patients with multiple sclerosis in whom efficacy has been demonstrated include patients who have experienced a first clinical episode and have MRI features consistent with MS.

The recommended dosage of Avonex® is 30 mcg injected intramuscularly once a week.

Study Duration

Screening phase: 1 month or up to 30 days.

Treatment phase: 24 months of once-daily oral administration of laquinimod 0.6 mg, matching oral placebo or once-weekly intramuscular administration of Interferon β-1a (Avonex®) 30 mcg.

Subjects successfully completing the study are offered the opportunity to enter into a 1-year open-label extension in which laquinimod 0.6 mg/d are administered.

A month is defined as 30±4 days in this study.

Number of Subjects

Approximately 1200 subjects.

Prior to the end of the recruitment period, a blinded relapse rate and sample size reassessment is performed. Based on the newly estimated relapse rate of the population, the sample size may be increased.

Dropouts are not replaced.

Study Design

Treatment Arms

Eligible subjects are randomized in a 1:1:1 ratio (oral laquinimod:oral placebo:Avonex®) and assigned to one of the following three treatment arms:

1. Laquinimod 0.6 mg per os once daily (400 subjects).
2. Matching placebo (for laquinimod) per os once daily (400 subjects).
3. Interferon β-1a (Avonex®) 30 mcg intramuscular injection once weekly (400 subjects).

Route and Dosage Form 0.6 mg arm: one capsule containing 0.6 mg laquinimod is administered orally once daily. The 0.6 mg laquinimod capsule contains 0.6 mg of Laquinimod Acid per capsule with meglumine.

The 0.6 mg laquinimod capsule is manufactured according to the method disclosed in PCT International Application Publication No. WO/2007/146248, published Dec. 21, 2007 (see, page 10, line 5 to page 11, line 3).

Matching placebo for laquinimod arm: one capsule is administered once daily.

Blinding

Subjects on oral treatment are managed in a double-blind manner. Subjects assigned to injectable treatment with Avonex® and their Treating Neurologist/Physician are unblinded to the treatment assignment, but assessed neurologically by an Examining Neurologist/Physician in a blinded manner (potential IM injection sites are covered).

Assessments at Specified Time Points

During the treatment phase, subjects are evaluated at study sites for a total of 12 scheduled visits at months: −1 (screening), 0 (baseline), 1, 2, 3, 6, 9, 12, 15, 18, 21 and 24 (termination/early discontinuation).

During the study, the following assessments are performed (regardless of the treatment assignment) at the specified time points:

1. Vital signs (temperature, pulse, blood pressure) are measured at each study visit.
2. A physical examination is performed at months −1 (screening), 0 (baseline) 1, 3, 6, 12, 18 and 24 (termination/early discontinuation).
3. The following safety clinical laboratory tests are performed:
   a. Hematology and Complete blood count (CBC) with differential—at all scheduled visits. A reticulocyte count is added to the CBC at months 0 (baseline) and 24 (termination/early discontinuation) as well as in occasions of significant decrease in hemoglobin.
   b. Serum chemistry (including electrolytes, liver enzymes, direct and total bilirubin, CPK and pancreatic amylase), and urinalysis—at all scheduled visits.
   c. Serum TSH, T3 and Free T4 are measured at months 0 (baseline), 6, 12, 18 and 24 (termination/early discontinuation).
   d. A rapid urine β-hCG test is performed in women of child-bearing potential at baseline (month 0; all subjects) and at each scheduled study visit thereafter (at site; only subjects assigned to oral treatment).

e. β-hCG in women of child-bearing potential are performed at each study visit.

f. Starting after visit Month 3 a rapid urine β-hCG test is performed in women of child-bearing potential (only those assigned to oral treatment) every 28 (±2) days. The subject is contacted by telephone with 72 hours after the test is scheduled to be performed and asked specific questions regarding the test. In case of suspected pregnancy (positive urine β-hCG test result), the caller makes sure that the study drug has been discontinued and the subject is instructed to arrive to the site as soon as possible with all study drugs.

4. Markers of inflammation (serum conventional C-reactive protein and fibrinogen) are measured at all scheduled visits.
5. Serum samples are collected for evaluation of immunological parameters and response to treatment with either laquinimod or Avonex®, as well as further investigation of the potential mechanisms of action of laquinimod or for the detection of infectious agents. These samples are collected at months 0, 12 and 24.
6. During the first 3 months of the study, periodical phone calls are placed by the site personnel every two weeks and fourteen (±2) days post month 1 and month 2 visits, the patient is asked questions relating to signs or symptoms suggestive of vascular thrombosis is presented to the subject and a list of predefined questions relating to signs/symptoms suggestive of vascular thrombosis is presented to the subject. In case of suspected thrombotic event, the subject is requested to arrive at the site immediately for further evaluation. Fourteen (±2) days post month 1 and month 2 visits, the patient is asked questions relating to signs or symptoms suggestive of vascular thrombosis is presented to the subject.
7. ECG is performed at months −1 (screening; additional recording, up to 30 minutes apart are performed if QTc is >450 msec), 0 (baseline; three recordings, 15 minute apart), 1, 2, 3, 6, 12, 18 and 24 (termination/early discontinuation).
8. Chest X-ray is performed at month −1 (screening) (if not performed within 6 months prior to screening visit).
9. Adverse Events (AEs) are monitored throughout the study and recorded.
10. Concomitant medications are monitored throughout the study.
11. Neurological evaluations, including Neurostatus [Functional Systems (FS), Expanded Disability Status Scale (EDSS; Converted scale), Ambulation Index (AI)] and Timed-25 foot walk test are performed at months −1 (screening), 0 (baseline) and every 3 months thereafter, until termination/early discontinuation. (At screening visit, the Timed-25 foot walk test is performed 3 times, for practicing purposes, as a part of the MSFC).
12. MS Functional Composite (MSFC) is assessed at months −1 (screening) (three practices for training purposes only), 0 (baseline), 6, 12, 18 and 24 (termination/early discontinuation).
13. The general health status is assessed by the EuroQoL (EQ5D) questionnaire at months 0 (baseline) and 24 (termination/early discontinuation).
14. The general health status and quality of life parameters are assessed by the Short-Form general health survey (SF-36) subject-reported questionnaire at month 0 (baseline) and every 6 months thereafter until termination/early discontinuation, inclusive.
15. Subject-reported fatigue is assessed by the Modified Fatigue Impact Scale (MFIS) at months 0 (baseline), 2, 6, 12, 18 and 24 (termination/early discontinuation).
16. All subjects undergo 3 MRI scans at months 0 (13-7 days prior to baseline visit), 12 and 24 (termination/early discontinuation). Subjects undergo MRI scan before and after Gadolinium administration (month 12).
17. All subjects undergo 5 assessment of binocular low-contrast visual acuity using the 1.25%, 2.5% and 100% contrast level charts [Sloan letter or Tumbling-E] in each assessment, at months 0 (baseline), 6, 12, 18 and 24 (termination/early discontinuation).
18. Blood test for Factor V Leiden mutation (FVLM) is performed at screening visit.
19. Serologies for Hepatitis B and C viruses are performed at screening visit.
20. Relapses are confirmed/monitored/evaluated throughout the study. Since the "in study" relapse definition must be supported by an objective neurological evaluation, a neurological deficit must sustain long enough to eliminate pseudo-relapses. Therefore, in Bravo, a confirmed relapse is the appearance of one or more new neurological abnormalities or the reappearance of one or more previously observed neurological abnormalities wherein the change in clinical state lasts at least 48 hours and is immediately preceded by an improving neurological state of at least thirty (30) days from onset of previous relapse.
21. The allowed treatment for a relapse is intravenous methylprednisolone 1 gr/day for up to 5 consecutive days.
22. Assessment of the effect of general health and symptom severity on work, using the work productivity and activities impairment—General Health (WPAI-GH) questionnaire (months 3, 6, 9, 12, 15, 18 and 21) (this assessment is performed in all subjects from US sites only).
23. The sequence of assessments performed during the visits is as follows:
    a. Short-Form general health survey (SF-36) subject-reported questionnaire (months 6, 12 and 18)
    b. Modified Fatigue Impact Scale (MFIS) (months 2, 6, 12 and 18)
    c. The work productivity and activities impairment General Health (WPAIGH) questionnaire (applicable only to US sites, months 3, 6, 9, 12, 15, 18 and 21)
    d. The 9-Hole Peg and PASAT components of the MSFC (Timed 25 Foot walk may be performed later) (months 6, 12 and 18)
24. The rest of the visit activities, as described above
25. For subjects who are assigned to oral treatment, the last dose of study drug is taken one day prior to the Termination visit day.
26. For subjects who are assigned to injections, the study drug (Avonex®) is not administered on Termination visit day.

Safety Parameters—Adverse Events

Adverse events are recorded from when a subject has signed the Informed Consent Form and throughout the study, until 30 days following the termination visit.

Safety Parameters—Safety Laboratory Evaluations

The following tests are performed:

1. Serum Chemistry: Glucose, Creatinine, Bilirubin (direct and total), Urea, AST (SGOT), ALT (SGPT), GGT, Pancreatic Amylase, Lipid profile (once in the study either at screening or baseline visits; 12-hours-fasting is mandatory: Total cholesterol, LDL cholesterol, HDL cholesterol and triglycerides), Total Protein Albumin, CRP (C reactive protein, conventional assay), Alkaline Phosphatase, CPK, T3, Free T4, and TSH [only at months 0 (baseline), 6, 12, 18 and 24 (termination/early discontinuation)].
2. Electrolytes: Sodium, Potassium, Calcium, and Phosphorous.
3. Coagulation: Fibrinogen and INR (performed in a local laboratory)
4. Hematology: Hemoglobin, MCH, MCV, MCHC, Hematocrit, Red Blood Cells count (RBC), White Blood Cells count+differential, Platelet count, and a reticulocyte count is added to the CBC at months 0 (baseline) and 24 (termination/early discontinuation visit), and in any case of a ≥2 g/dL decrease in hemoglobin, as compared to baseline level. In such cases, measurement of reticulocyte count continues with each CBC test until the difference between hemoglobin value and baseline hemoglobin is <2 g/dL.
5. Factor V Leiden Mutation: This sample (for this mutation only) is collected at screening visit and stored frozen in the central laboratory. This sample may be analyzed upon request of the DMC at any time during the study. If, from any reason, the subject is a screening failure, this sample is destroyed.
6. Pregnancy tests
7. Urinalysis: glucose, ketones, erythrocytes, leukocytes and protein
8. Serology (to be performed only for a confirmed abnormality of liver enzymes): anti-Hepatitis A IgM antibodies, hepatitis B Surface antigen, anti-Hepatitis B Core IgM antibodies, anti-Hepatitis C IgG antibodies, anti-nuclear antibodies, anti-Smooth Muscle (Sm) antibodies, and anti-Liver-Kidney Microsomes (LKM)-1 antibodies Safety and Pharmacovigilance A new condition or the worsening of a pre-existing condition is considered an AE. Stable chronic conditions that are present prior to study entry and does not worsen during the study are not considered AEs.

The date of onset, a description of the AE, severity, seriousness, action taken, relationship to the study drug, outcome of the event and date of resolution is recorded.

Ancillary Studies

Pharmacogenetic (PGt) assessment: Upon the approval of this ancillary study by EC/IRB, blood samples for PGt parameters are collected from all subjects who signed the informed consent form at month 0 (baseline).

Relationship between PGt and response to laquinimod or to Avonex® in terms of clinical, MRI and safety parameters is assessed in all sites.

The effect of general health and symptom severity on work is assessed by the work productivity and activities impairment-General Health (WPAI-GH) questionnaire at month 0 (baseline) and every 3 months thereafter, until month 24 (termination/early discontinuation) visit (this assessment is performed in all subjects from the U.S. sites only).

Inclusion/Exclusion Criteria
Inclusion Criteria
1. Subjects must have a confirmed and documented MS diagnosis as defined by the Revised McDonald Criteria [Ann Neurol 2005:58:840-846], with a relapsing-remitting disease course.
2. Subjects must be ambulatory with Converted EDSS score of 0-5.5 in both screening and baseline visits.
3. Subjects must be in a stable neurological condition and free of corticosteroid treatment [intravenous (IV), intramuscular (IM) and or per os (PO)] 30 days prior to screening (month −1) and between screening (month −1) and baseline (month 0) visits.
4 Subjects must have had experienced one of the following:
 a. At least one documented relapse in the 12 months prior to screening, or
 b. At least two documented relapses in the 24 months prior to screening, or
 c. One documented relapse between 12 and 24 months prior to screening with at least one documented T1-Gd enhancing lesion in an MRI performed within 12 months prior to screening.
5. Subjects must be between 18 and 55 years of age, inclusive.
6. Women of child-bearing potential must practice an acceptable method of birth control. Acceptable methods of birth control in this study include: surgical sterilization, intrauterine devices, oral contraceptive, contraceptive patch, long-acting injectable contraceptive, partner's vasectomy or a double-barrier method (condom or diaphragm with spermicide).
7. Subjects must be able to sign and date a written informed consent prior to entering the study.
8. Subjects must be willing and able to comply with the protocol requirements for the duration of the study.

Exclusion Criteria
1. An onset of relapse or any treatment with corticosteroid (intravenous [IV], intramuscular [IM] and/or per os [PO]) or ACTH between month −1 (screening) and 0 (baseline).
2. Subjects with progressive forms of MS.
3. Use of experimental or investigational drugs, and/or participation in drug clinical studies within the 6 months prior to screening.
4. Use of immunosuppressive (including Mitoxantrone (Novantrone®)) or cytotoxic agents within 6 months prior to the screening visit.
5. Previous use of either of the following: natalizumab (Tysabri®), cladribine, laquinimod, Interferon beta-1a (Avonex® or Rebif®), Interferon beta beta-1b (Betaseron®/Betaferon®) or any other experimental Interferon-beta for MS.
6. Previous treatment with glatiramer acetate (Copaxone®) or IVIG within 2 months prior to screening visit.
7. Chronic (more than 30 consecutive days) systemic (IV, PO or IM) corticosteroid treatment within 2 months prior to screening visit.
8. Previous total body irradiation or total lymphoid irradiation.
9. Previous stem-cell treatment, autologous bone marrow transplantation or allogenic bone marrow transplantation.
10. A known history of tuberculosis.
11. Acute infection within 2 weeks prior to baseline visit.
12. Major trauma or surgery within 2 weeks prior to baseline visit.
13. Known human immunodeficiency virus (HIV) positive status.
14. Use of inhibitors of CYP3A4 within 2 weeks prior to baseline visit.
15. Use of amiodarone within 2 years prior to screening visit.
16. Pregnancy or breastfeeding.
17. A ≥3×ULN serum elevation of either ALT or AST at screening.
18. Serum direct bilirubin which is ≥2×ULN at screening.
19. A QTc interval which is >450 msec (according machine output), obtained from:
 a. Two ECG recordings at screening visit, or
 b. The mean value calculated from 3 baseline ECG recordings.

20. Subjects with a clinically significant or unstable medical or surgical condition that, in the Investigator's opinion, would preclude safe and complete study participation, as determined by medical history, physical examination, ECG, laboratory tests or chest or chest X-ray. Such conditions may include:
   a. A cardiovascular or pulmonary disorder that cannot be well-controlled by standard treatment permitted by the study protocol.
   b. A gastrointestinal disorder that may affect the absorption of study medication.
   c. Renal, metabolic or hematological diseases.
   d. Thyroid disease: a subject with hyperthyroidism is not permitted to participate in the study. A subject with hypothyroidism may be permitted to participate in the study provided that he/she is clinically euthyroid and considered stable.
   e. Liver disease, such as cirrhosis.
   f. A family history of Long-QT syndrome.
   g. A history of drug and/or alcohol abuse.
   h. A current major psychiatric disorder, including schizophrenia or severe depression, with or without suicidal ideation.
   i. A history of seizure disorder, with the last convulsion occurring within 12 months prior to screening visit.
21. A known history of sensitivity to Gadolinium.
22. Inability to successfully undergo MRI scanning.
23. A known drug hypersensitivity that would preclude administration of laquinimod, such as hypersensitivity to: mannitol, meglumine or sodium stearyl fumarate.
24. A known history of hypersensitivity to natural or recombinant interferon beta, human albumin, or any other component of the formulation of Avonex®.

Additional disallowed concomitant medications/therapies: interferons, glatiramer acetate) (Copaxone®), Natalizumab (Tysabri®), inhibitors of CYP3A4, Mitoxantrone (Novantrone®), oral steroids, parenteral steroids (except as given as allowed for treatment of an acute relapse), chemotherapeutic agents, 4-amino pyridine or 3,4 diaminopyridine, IV Immunoglobulin (Ig) and any other experimental agents, and other Immunosuppressive or immunomodulating agents.

A partial list of CYP3A4 inhibitors (disallowed 2 weeks prior and during treatment period) is listed below:

Cardiac drugs/antiarrhythmic agents such as amiodaronec, diltazem, nifedipine, verapamil, or mibefradil; Antimicrobial agents such as Erythromycin, Clarithromycin, Troleandomycin, Telithromycin, Fluconazole, Itraconazole, Ketoconazole, Miconazole, or Voriconazole; HIV drugs such as Delavirdine or Protease Inhibitors, such as indinavir, ritonavir and others; Antidepressants such as fluoxetine, fluvoxamine, or nefazodone; and other CYP3A4 inhibitors such as isoniazid, quinine, cimetidine, zileuton, or aprepitant.

Statistical Considerations

The sample size considerations for the study are based on the following assumptions:
1. An individual subject's number of confirmed relapses during a one year period reflects a Poisson process with an individual rate of λi, and this individual subject rates λi are exponentially distributed with mean 1/θ, where θ is the population's annualized relapse rate. This approach models the total number of confirmed relapses as an Over Dispersed Poisson distribution.
2. The expected annualized relapse rate in an untreated patient population is θ=0.65 relapses per year.
3. In the placebo treatment group, the expected annualized relapse rate is θ=0.6 relapses per year, due to a placebo effect.
4. Treatment with laquinimod reduces the patient population annualized relapse rate by 25% or more when compared to the placebo group. That is, the expected annualized relapse rate of the laquinimod treated population is θ=0.45 relapses per year or less.

A simulation study accounting for the above underlying assumptions used the Quasi-likelihood (over-dispersed) Poisson regression (SAS® PROC GENMOD), revealed that a total of 666 subjects (333 subjects per arm) provides approximately 80% power to detect a statistically significant reduction of 25% in the total number of confirmed relapses between the placebo group and the laquinimod group. This sample size also enables 92% power to detect a statistically significant reduction of 30% in the total number of confirmed relapses between the laquinimod 0.6 mg treatment group and the placebo group.

The analysis of the total numbers of confirmed relapses during the treatment period is based on baseline adjusted Quasi-Likelihood (over-dispersed) Poisson Regression. The analysis of disability as assessed by MSFC at the end of the treatment period, and the analysis of brain atrophy as defined by the percent brain volume change from baseline to the end of the treatment period is based on the baseline adjusted Analysis of Covariance. The analysis of the accumulation of physical disability measured by the time to a confirmed progression of EDSS is based on Cox' Proportional Hazard model.

Route and Dosage Form

Laquinimod Arm:
one capsule containing laquinimod 0.6 mg is administered orally once daily, preferably at the same hour every day with a glass of water.

The 0.6 mg laquinimod capsule is manufactured according to the method disclosed in PCT International Application Publication No. WO/2007/146248, published Dec. 21, 2007 (see, page 10, line 5 to page 11, line 3).

Matching Placebo for Laquinimod Arm:
one capsule is administered orally once daily, preferably at the same hour every day with a glass of water.

Avonex® Arm:
one injection of Interferon β-1a (Avonex®) 30 mcg is administered intramuscularly once weekly, preferably on the same day.

Outcome Measures

Primary Outcome Measure

The number of confirmed relapses during the treatment period.

Secondary Outcome Measures

Type-I error is controlled by employing the Hierarchical Approach, (i.e. each endpoint is analyzed only in case the preceding endpoint has a p-value less or equal to 0.05 for laquinimod 0.6 mg over placebo comparison) according to the following order:
1. Disability, as assessed by the MSFC score at the end of the treatment period.
2. Brain atrophy as defined by the percent brain volume change from baseline at the end of the treatment period.
3. Accumulation of physical disability measured by the time to confirmed progression of EDSS (A confirmed progression of EDSS is defined as a 1 point increase from baseline on EDSS score if baseline was between 0 and 5.0, or a 0.5 point increase if baseline EDSS was 5.5, confirmed 3 months later. Progression cannot be confirmed during a relapse).

Safety and Tolerability Outcome Measures
1. Adverse events.
2. Vital signs.
3. ECG findings.
4. Clinical laboratory parameters.
5. Proportion of subjects (%) who prematurely discontinued from the study, reason of discontinuation and the time to withdrawal.
6. Proportion of subjects (%) who prematurely discontinued from the study due to AEs and the time to withdrawal.

Benefit/Risk Assessment

The Avonex® reference arm is compared to the placebo treatment group with respect to the same endpoints as for the comparison between the laquinimod group and the placebo group.

These endpoints include:
1. The number of confirmed relapses during the treatment period.
2. Disability measures based on EDSS and MSFC neurological scales.
3. MRI parameters.
4. Safety as assessed by adverse events, vital signs, ECG and clinical laboratory parameters.
5. Tolerability
6. Quality of life scales such as: Modified Fatigue Impact Scale (MFIS), General health status, as assessed by the EuroQoL (EQ5D) questionnaire and the Short-Form general Health survey (SF-36) subject-reported questionnaire.

The comparative assessment of the benefit/risk ratio between the two active arms (laquinimod and Avonex®) is based on the following aspects:
1. Efficacy parameters (Disability, MRI parameters, other relapse-related endpoints).
2. Safety and tolerability.
3. Quality of life.

Additional Exploratory Endpoints

The following assessments are presented in an exploratory manner:
1. The total number of enhancing lesions on T1-weighted images taken at months 12 and 24 (termination/early discontinuation).
2. The number of enhancing lesions on a T1-weighted image taken at month 12.
3. The number of enhancing lesions on a T1-weighted image taken at month 24 (termination/early discontinuation).
4. The total number of new hypointense lesions ("black holes") on enhanced T1 scans taken at months 12 and 24 (termination/early discontinuation).
5. The total number of new hypointense lesions ("black holes") on an enhanced T1 scan taken at month 12.
6. The total number of new hypointense lesions ("black holes") on an enhanced T1 scan taken at month 24 (termination/early discontinuation).
7. The total number of new/newly enlarging T2 lesions on scans taken at months 12 and 24 (termination/early discontinuation).
8. The number of new/newly enlarging T2 lesions on a scan taken at month 12.
9. The total number of new/newly enlarging T2 lesions on scans taken at month 24 (termination/early discontinuation).
10. The change in T2-lesion volume between months 0 (baseline) and 24 (termination/early discontinuation).
11. The volume of T-2 lesions at termination/early discontinuation of treatment period.
12. The change from baseline to month 24 (termination/early discontinuation) in the volume of hypointense lesions on enhanced T1 scans.
13. Brain atrophy as defined by the percent brain volume change from: 1) baseline to month 12 and b) month 12 to month 24 (termination/early discontinuation).
14. The change from baseline to month 24 (termination/early discontinuation) in binocular visual acuity, as assessed by the number of letters read correctly from 2 meters distance on 1.25%, 2.5% and 100% contrast level Sloan letter/Tumbling-E charts.
15. Subject-reported fatigue, as assessed by the Modified Fatigue Impact Scale (MFIS).
16. The time to the first confirmed relapse during the treatment period.
17. The proportion of relapse-free subjects.
18. The rate of confirmed relapses during the treatment period requiring hospitalization and/or IV steroids.
19. The general health status, as assessed by the EuroQoL (EQ5D) questionnaire.
20. The general health status and health-related quality of life, as assessed by the Short-Form general health survey (SF-36) subject-reported questionnaire.

Assessment Methods

Neurostatus—A complete neurological assessment is performed at months −1 (screening), 0 (baseline) and every 3 months thereafter until termination/early discontinuation of the study. The neurological assessment is a standardized neurological examination and assessment of Kurtzke's functional systems and expanded disability status.

The MS Functional Composite consists of 3 clinical examinations, the results of which are combined using z-scores. The three clinical examinations include the PASAT, Timed 25 Foot walk and 9-Hole Peg Test. The PASAT and 9-Hole Peg tests are performed at months −1 (screening) (only for training purposes), 0 (baseline), 6, 12, 18 and 24 (termination/early discontinuation) visits. The Timed 25 Foot walk test is performed each time the Neurostatus is performed.

The low-contrast visual acuity is assessed binocularly at months 0 (baseline), 6, 12, 18 and 24 (termination/early discontinuation) visits, along with the MSFC assessments.

All subjects undergo 3 MRI scans (before and after gadolinium administration) at months: 0 (baseline), 12 and 24 (termination/early discontinuation). The following parameters are assessed on each relevant scheduled scan:

Number of Gd-enhancing lesions on T1-weighted MRI scans, number of new/newly enlarging $T_2$ hyperintense lesions (with reference to the previous scan), volume of T9 hyperintense lesions, number of new hypointense lesions on gadolinium-enhanced $T_1$-weighted MRI scans ('black holes') (with reference to the previous scan), volume of hypointense lesions on gadolinium-enhanced $T_1$-weighted MRI scans, percent brain volume change (with reference to previous scan), and normalized brain volume (at baseline). All MRI data is evaluated and quantified by the MRI-AC.

Subject-reported fatigue assessed by the Modified Fatigue Impact Scale (MFIS) at months 0, 2, 6, 12, 18 and 24 (termination/early discontinuation).

The general health status is assessed by the EuroQoL (EQ5D) questionnaire at months 0 (baseline) and 24 (termination/early discontinuation).

The general health status is also assessed by the Short-Form general health survey (SF-36) subject-reported questionnaire at month 0 (baseline) and every 6 months thereafter, until termination/early discontinuation. The SF-36 is a generic, self-administered health-related quality of life instrument. In this study the instrument is self-administrated during the visit.

Pharmacogenetic (PGt) assessment (ancillary study) is performed using an 8.5 ml blood sample taken at baseline visit.

Economic Impact is assessed by the Work Productivity and Activities Impairment (WPAIGH) Questionnaire (Ancillary Study, US sites only). The WPAI-GH was developed for assessing productivity losses by measuring the effect of general health and symptom severity on work as well as usual activity productivity. This questionnaire is administered at month 0 (baseline) and every 3 months thereafter, until month 24 (termination/early discontinuation) visit. This assessment is performed in all subjects from US sites only.

Serum samples are collected from all subjects at months 0 (baseline), 12 and 24 (termination/early discontinuation). They are collected for evaluation of immunological parameters and response to treatment with either laquinimod or Avonex®, as well as for further investigation of the potential mechanism of action of laquinimod.

Vital signs (temperature, pulse and blood pressure) are measured at all scheduled and unscheduled visits. At baseline visit, blood pressure and pulse are measured 30 and 60 minutes after the first drug administration. Blood pressure and pulse are recorded in a sitting position after resting for 5 minutes.

Weight is measured at screening and month 24 (termination/early discontinuation) visits. Height is measured at month −1 (screening) visit only.

ECGs are performed at months −1 (screening) (additional recording, up to 30 minutes apart are performed if QTc is >450 msec according to the machine output), 0 (baseline), 1, 2, 3, 6, 12 18 and 24 (termination/early discontinuation). At baseline visit, three ECGs are performed at 15 minutes intervals to serve as integrated baseline ECG, by averaging baseline interval results for comparison to on-treatment values.

The subject rests for at least 10 minutes before measurement is taken. Twelve-lead ECG is performed following the subject being in a supine position for 5 minutes.

A physical examination is performed at months −1 (screening), 0 (baseline) 1, 3, 6, 12, 18 and 24 (termination/early discontinuation).

A chest X-ray is performed at screening (month −1) if not performed within 6 months prior to screening and provided a report thereof can be obtained.

Results

Results from the BRAVO trial was reported in an Aug. 1, 2011 Press Release from Teva Pharmaceutical Industries, Ltd., and in Vollmer et al. (Neurology, Apr. 24, 2012; 78 (Meeting Abstracts 1):S01.007), the entire contents of each of which are hereby incorporated by reference into this application.

Example 3

Post Hoc Analysis of ALLEGRO and BRAVO Trials: Evaluation of Laquinimod Efficacy in Patient Subgroups Introduction Natural history data show that once EDSS of 3 is reached, disability progression becomes both more likely and more rapid (Pittock et al. Neurology 2004; 62:51-9; Pittock et al. Neurology 2004; 62:601-6; Leray et al. Brain 2010; 133: 1900-1913). At EDSS>3, chronic diffuse inflammation may be a more important driver of disability.

Patients with an EDSS score of ≤3 are fully ambulatory; however gait dysfunction is common in multiple sclerosis and is a key component of disability progression beyond this stage. Patients beyond this stage experience growing motor impairment. Patients with an EDSS of 3.5 are fully ambulatory but already manifest moderate disability in selected functional systems. Patients with an EDSS of 4 experience some restriction in ambulation, but are up and about most of the day despite clear neurological dysfunction. Subsequent EDSS progression is characterized by objective declines in ambulation and relatively severe disability in other functional domains.

RRMS patients who have demonstrated disease worsening ("worsening MS") (Lublin, 2014) and reached an EDSS over 3 may experience confirmed disability progression (CDP) more detrimental to daily function than progression from lower EDSS steps. The clinical need may be addressed by laquinimod treatment, which significantly reduced annualized relapse rate (ARR) and to a greater extent, CDP vs. placebo (PBO) in the phase III ALLEGRO and BRAVO studies. Laquinimod reduced EDSS-based CDP overall and in EDSS subgroups.

Summary

Nonclinical and clinical data support that laquinimod exerts a direct protective effect within the central nervous system, partly independent of its peripheral anti-inflammatory effects. The efficacy profile of oral Laquinimod (LAQ) 0.6 mg daily, demonstrated by ALLEGRO and BRAVO studies described in Examples 1 and 2, respectively, differs from that of other RRMS therapies. The observed effect of LAQ on Confirmed Disability Progression (CDP) is disproportionately larger than would be predicted by the observed LAQ effect on relapse rate reduction. This study investigates the effects of laquinimod 0.6 mg once-daily treatment on individual Multiple Sclerosis Functional Composite (MSFC) components in the pooled ALLEGRO and BRAVO patient subgroups with baseline (BL) EDSS over 3, with aim to associate changes in T25FW and EDSS in this worsening RRMS population at risk for progressive disease.

In pooled data from the Phase III ALLEGRO and BRAVO studies of oral laquinimod (LAQ) 0.6 mg once-daily (QD) vs. placebo (PBO) in RRMS, a 46% reduction in 6-month confirmed disability progression (CDP) (Vollmer, ECTRIMS 2011) was not accompanied by a significant treatment (Tx) effect on the Multiple Sclerosis Functional Composite (MSFC). However, for a subgroup of LAQ-treated patients with worsening MS (EDSS>3 at baseline [BL]), a 53% reduction in 6-month CDP was accompanied by a significant MSFC effect (mean z-score difference, 0.25) vs. PBO.

Methods

ALELGRO and BRAVO trials described above enrolled ambulatory patients with RRMS, aged 18-55 years, with EDSS scores ≤5.5. Patients included in the study had
1. ≥1 relapse in the previous year, or
2. 2 relapses in the previous 2 years, or
3. 1 relapse in the previous 1-2 years and ≥1 GdE lesion in the previous year.

Patients were randomized 1:1 to LAQ 0.6 mg or PBO in the ALLEGRO study; in BRAVO patients were randomized 1:1:1 LAQ 0.6 or PBO or weekly interferon β 1a 30 μg.

Pooled data from ALLEGRO and BRAVO (Total N=1990; LAQ 0.6 mg QD N=984; PBO N=1006) trials were used in this post hoc analysis, in which laquinimod efficacy was evaluated in patient subgroups; in particular the two patient subgroups: patients having baseline EDSS≤3, and patients having baseline EDSS>3. This post hoc analysis include patients randomized to LAQ 0.6 mg or PBO only. Endpoints include ARR, time to CDP (defined as an increase from baseline in EDSS score of ≥1 point if baseline EDSS is ≤5, or of ≥0.5 point if baseline EDSS is >5), sustained for 3 or 6 months; and MSFC components including the Timed 25-Foot Walk (T25FW) test.

LAQ vs. PBO treatment effects on change in MSFC subscores at 24 months for the Paced Auditory Serial Addition Test (PASAT), 9-Hole Peg Test (9HPT), and T25FW, in patients with EDSS>3 at baseline were assessed. Adjusted mean z-score differences and 95% CIs were evaluated by ANCOVA.

MRI endpoints included brain atrophy measured percent brain volume change (PBVC), and cumulative numbers of gadolinium-enhancing (GdE) and new T2 lesions at months 12 and 24.

Baseline statistics of the patients are shown in Table 5 below:

| Pooled ALLEGRO and BRAVO | EDSS ≤ 3 (N = 1335) | | | EDSS > 3 (N = 655) | | |
|---|---|---|---|---|---|---|
| | Placebo (n = 679) | LAQ 0.6 mg (n = 656) | Total | Placebo (n = 327) | LAQ 0.6 mg (n = 328) | Total |
| Age (years), mean ± SD | 36.5 ± 9.2 | 36.4 ± 9.1 | 36.5 ± 9.1 | 41.3 ± 8.5 | ±41.3 ± 8.9 | 41.3 ± 8.7 |
| Weight (kg) ± Mean SD | 71.8 ± 15.8 | 70.2 ± 16.0 | | 70.1 ± 15.2 | 70.6 ± 16.1 | |
| BMI (kg/m$^2$) ± Mean SD | 24.9 ± 5.2 | 24.6 ± 5.1 | | 24.9 ± 49 | 24.8 ± 5.2 | |
| Female Gender, N (%) | 460 (67.7%) | 450 (68.6%) | 910 (68.2%) | 229 (70.0%) | 223 (68.0%) | 452 (69.0%) |
| Previous MS treatment, N(%) | 176 (25.9%) | 149 (22.7%) | 325 (24.3%) | 72 (22.0%) | 91 (27.7%) | 163 (24.9%) |
| EDSS at baseline, mean ± SD | 2.0 ± 0.7 | 1.9 ± 0.7 | 1.9 ± 0.7 | 4.1 ± 0.7 | 4.1 ± 0.6 | 4.1 ± 0.7 |
| Time from MS diagnosis (years), mean ± SD | 3.8 ± 4.8 | 3.6 ± 4.4 | 3.7 ± 4.6 | 4.8 ± 5.0 | 5.6 ± 5.5 | 5.2 ± 5.3 |
| Time from first symptom (years), mean ± SD | 7.0 ± 6.2 | 6.8 ± 6.1 | 6.9 ± 6.1 | 9.7 ± 7.3 | 9.8 ± 7.0 | 9.7 ± 7.2 |
| Number of Relapses in 1 year prior to screening (MEAN ± SD) | 1.3 ± 0.7 | 1.2 ± 0.6 | | 1.3 ± 0.7 | 1.3 ± 0.7 | |
| Number of Relapses in 2 years prior to screening (MEAN ± SD) | 1.8 ± 0.9 | 1.8 ± 0.9 | | 2.0 ± 1.0 | 2.0 ± 1.1 | |
| GdE lesions > 0 at Baseline, N (%) | 271 (39.9%) | 267 (40.7%) | | 133 (40.7%) | 126 (38.4%) | |
| Number of GdE T1 lesions, mean ± SD | 1.4 ± 3.8 | 1.7 ± 4.5 | 1.5 ± 4.2 | 2.5 ± 8.3 | 1.9 ± 4.6 | 2.2 ± 6.7 |
| Volume of T2 lesions (cm$^3$), mean ± SD | 7.5 ± 8.1 | 8.2 ± 9.2 | 7.8 ± 8.7 | 11.8 ± 12.2 | 12.8 ± 11.8 | 12.3 ± 12.0 |
| Baseline brain volume, mean ± SD | 1609 ± 89.2 | 159 ± 90.8 | 1601 ± 90.0 | 1551 ± 90.5 | 1542 ± 91.0 | 1547 ± 90.8 |

Overall, 655 patients (33%; LAQ n=328, PBO n=327) had baseline EDSS>3; mean (SD) baseline EDSS was 4.1 (0.7). One-fourth (24.9%) had received prior MS treatment. Compared with the EDSS≤3 subgroup, patients with baseline EDSS>3 were older (mean age 41.3 vs. 36.5 years), had longer disease duration (5.2 vs. 3.7 years), more GdE lesions, larger T2 lesions, and lower brain volume (1547 vs. 1601 cm$^3$) at baseline.

Results

Results from this post hoc analysis is shown in Table 6 below:

| | | EDSS ≤3.0 LAQ 0.6 mg, n = 656 (66.7%) PBO, n = 679 (67.5%) | EDSS >3.0 LAQ 0.6 mg, n = 328 (33.3%) PBO, n = 327 (32.5%) |
|---|---|---|---|
| Annualized Relapse Rate | Ratio [CI] | 0.80 [0.67; 0.95]; p = 0.0103 | 0.75 [0.60; 0.94]; p = 0.0119 |

-continued

|  |  | EDSS ≤3.0<br>LAQ 0.6 mg, n = 656<br>(66.7%)<br>PBO, n = 679<br>(67.5%) | EDSS >3.0<br>LAQ 0.6 mg,<br>n = 328 (33.3%)<br>PBO, n = 327<br>(32.5%) |
|---|---|---|---|
| Time to 3-month CDP | Hazard Ratio[CI] | 0.69<br>[0.50; 0.96];<br>p = 0.0256 | 0.60<br>[0.38; 0.93];<br>p = 0.0229 |
| Time to 6-month CDP | Hazard Ratio[CI] | 0.60<br>[0.41; 0.88];<br>p = 0.0088 | 0.47<br>[0.27; 0.82];<br>p = 0.0083 |
| Disability as Assessed by MSFC z-Score at Month 24 | Adjusted mean difference [CI] | −0.02<br>[−0.12; 0.09];<br>p = 0.7614 | 0.25<br>[0.10; 0.39];<br>p = 0.0009 |
| Brain Atrophy as defined by PBVC | Adjusted mean difference [CI] | 0.34<br>[0.21; 0.47];<br>p < 0.0001 | 0.39<br>[0.21 0.58];<br>p < 0.0001 |
| Cumulative GdE T1 Lesions at Months 12 and 24 | Rate Ratio[CI] | 0.66<br>[0.53; 0.82];<br>p = 0.0002 | 0.83<br>[0.61; 1.13];<br>p = 0.2390 |
| Cumulative New/Enlarging T2 Lesions at Months 12 and 24 | Rate Ratio[CI] | 0.77<br>[0.65; 0.91];<br>p = 0.0024 | 0.75<br>[0.59; 0.96];<br>p = 0.0214 |
| T25FW Change from Baseline to Month 24 | Adj. Mean Diff.<br>Confidence Interval<br>p-value | 0.055<br>[−1.250; 1.359]<br>0.9342 | −2.79<br>[−4.664; −0.917]<br>0.0035 |
| PASAT Change from Baseline to Month 24 | Adj. Mean Diff.<br>Confidence Interval<br>p-value | 0.302<br>[−0.4670; 1.071]<br>0.4411 | 0.586<br>[−0.515; 1.687]<br>0.2967 |
| 9HPT Change from Baseline to Month 24 | Adj. Mean Diff.<br>Confidence Interval<br>p-value | −1.108<br>[−3.041; 0.681]<br>0.2137 | −1.590<br>[−4.257; 1.077]<br>0.2425 |

In the subgroup of RRMS patients with BL EDSS>3, LAQ significantly reduced ARR (25%, p=0.012); 3-month CDP (40%, p=0.0083), 6-month CDP (53%, p=0.0009), and MSFC worsening (mean z-score difference of 0.25, p=0.0009). Improvement on the MSFC was driven by a 59% improvement with LAQ on the T25FW component vs. PBO in these patients. LAQ also significantly reduced PBVC (adjusted mean Tx difference 0.39 [95% CI 0.21, 0.58]; p<0.0001), and cumulative number of new T2 lesions (rate ratio 0.75 [95% CI 0.59, 0.96]; p=0.021) vs PBO. LAQ treatment effect on cumulative number of GdE lesions was not statistically demonstrated in this subgroup (rate ratio 0.83 [0.61, 1.13]; p=0.24).

MSFC Components

The difference between the results for Timed 25-Foot Walk (T25FW) test for the two patient subgroups (EDSS≤3 and EDSS>3) is most pronounced. Among MSFC components, only the T25FW demonstrated a statistically significant LAQ effect (p=0.0035) in the subgroup with BL EDSS>3. (See Table 6)

At baseline, subjects in the EDSS≤3 group completed the Timed 25-Foot Walk in a mean (SD) of 5.40±5.3 seconds, and subjects in the EDSS>3 group completed the T25FW in 8.29±6.81 seconds. A 59% LAQ Tx effect on mean [SE] T25FW time (−2.79 [0.96] seconds, 95% CI−4.66, −0.92; p=0.0035) appeared to drive the overall MSFC benefit in the EDSS>3 subgroup as shown in FIG. 1. However, directional change consistent with a LAQ effect on the PASAT and 9HPT are present.

No treatment differences were seen in T25FW amongst subjects with EDSS≤3. In contrast, subjects with EDSS>3 who received placebo increased their T25FW time by 4.7 seconds (adjusted mean, 95% CI 3.2-6.2) after 24 months, while T25FW increase was 1.9 seconds (95% CI 0.5-3.4) in subjects treated with laquinimod (p=0.004; interaction p=0.01; effect size=59%). Thus, the significant effect on ambulation appears unique to the EDSS>3 subpopulation.

Association Between T25FW and EDSS Changes

An interaction between LAQ treatment effect on T25FW and CDP was found: there was a significant interaction (p<0.0001), whereby the T25FW treatment effect was 8.6 seconds among subjects with EDSS>3 who experienced CDP.

Among patients who experienced 3-month CDP during the trial, the T25FW markedly increased from baseline to 24 months in the EDSS>3 subgroup (mean change [SD]=12.3 [±34.7] seconds, n=74). Patients in the EDSS≤3 subgroup had little T25FW change, despite having CDP according to the EDSS (mean change [SD]=0.4 [±21.0] seconds, n=140). This finding is consistent with the notion that EDSS progression beyond 3 is associated with ambulatory dysfunction.

There was little T25FW change among patients who did not experience CDP (mean change [SD]=0.90 [±9.3] seconds in the EDSS>3 group and 0.16 [5.9] seconds in the EDSS≤ subgroup).

A significant three-way subgroup×treatment×CDP interaction was found. That is, the LAQ treatment effect on the T25FW was accentuated in patients with EDSS>3 who experienced CDP. PBO-treated patients who experienced CDP beyond an EDSS of 3 declined 8.6 seconds more than equivalent LAQ-treated patients (FIG. 2).

T25FW data support the effect of laquinimod on CDP as an independent, relevant assessment in patients with EDSS greater than 3.

Conclusion

Laquinimod demonstrated significant benefits in relapse, disability, and MRI outcomes in patients with baseline EDSS>3.

A 53% reduction in 6-month CDP was observed in this worsening MS subgroup, and its specific clinical meaningfulness is evidenced by a 59% T25FW ambulation benefit. These findings support the notion of an imminent risk of disability progression marked by ambulatory decline in patients who have reached an EDSS score above 3.

Laquinimod is associated with substantial benefit on ambulatory function, producing clinically meaningful reductions in T25FW change amongst those with baseline EDSS>3.

The treatment effect was heightened in those in this subgroup who experienced CDP.

REFERENCES

1. Barkhof, F. (1999) "MRI in Multiple Sclerosis: Correlation with Expanded Disability Status Scale (EDSS)", *Multiple Sclerosis.* 5(4):283-286 (Abstract).
2. Bjartmar and Fox (2002) "Pathological mechanisms and disease progression of multiple sclerosis: therapeutic implication", *Drugs of Today.* 38:7-29.
3. Brex et al. (2002) "A longitudinal study of abnormalities on MRI and disability from multiple sclerosis", *N Engl J Med.* Jan. 17, 2002 346(3):158-64.
4. Brunmark et al. (2002) "The new orally active immunoregulator laquinimod (ABR-215062) effectively inhibits development and relapses of experimental autoimmune encephalomyelitis", *J Neuroimmunology.* 130:163-172.
5. Clinical Trials Website, retrieved on Mar. 30, 2015 from <https://clinicaltrials.gov/ct2/show/NCT01328379?term=six+-minute+walk&cond=multiple+sclerosis&rank=1>.
6. Cohen et al. (2010) "Oral fingolimod or intramuscular interferon for relapsing multiple sclerosis". *N Eng J Med;* 362:402-415.
7. Comi et al. (2007) LAQ/5062 Study Group. "The Effect of Two Doses of Laquinimod on MRI-Monitored Disease Activity in Patients with Relapsing-Remitting Multiple Sclerosis: A Multi-Center, Randomized, Double-Blind, Placebo-Controlled Study", Presented at: 59*th Annual Meeting of the American Academy of Neurology*; Apr. 28-May 5, 2007; Boston, Mass.
8. Comi et al. (2008) "Effect of laquinimod on MRI-monitored disease activity in patients with relapsing-remitting multiple sclerosis: a multicentre, randomised, double-blind, placebo-controlled phase IIb study", *Lancet.* 371:2085-2092.
9. Comi et al. (2009) for the LAQ/5062 Clinical Advisory Board and Study Group. Long-term open extension of oral laquinimod in patients with relapsing multiple sclerosis shows favorable safety and sustained low relapse rate and MRI activity. [Ectrims abstract P443]. *Mult Scler.* 15(Suppl 2):S127.
10. Comi et al. (2010) for the LAQ/5062 Clinical Advisory Board and Study Group. The effect of laquinimod on MRI-monitored disease activity in patients with relapsing-remitting multiple sclerosis: a double-blind active extension of the multicentre, randomised, double-blind, parallel-group placebo-controlled study. *Mult Scler.* 16:1360-1366.
11. Comi G et al. (2012) N Engl J Med; 366:1000-1009.
12. Comi G et al. (2014) Neurology; 82(Suppl):P3.195.
13. Comi G et al. (2014) Neurology; 82(Suppl):S4.001.
14. Cutter et al. (1999) "Development of a multiple sclerosis functional composite as a clinical trial outcome measure", *Brain.* 122:871-882.
15. De Stefano et al. (1999) "Evidence of early axonal damage in patients with multiple sclerosis", *Neurology.* 52(Suppl 2):A378.
16. Dunitz. M. (1999) *Multiple sclerosis therapeutics*, Ed. Rudick and Goodkin. London: Taylor & Francis, 1999.
17. Durelli et al. and the Independent Comparison of Interferon (INCOMIN) Trial Study Group. (2002) "Every-other-day interferon beta-1b versus once-weekly interferon beta-1a for multiple sclerosis: results of a 2-year prospective randomised multicentre study (INCOMIN)", *Lancet.* 359:1453-60.
18. EMEA Guideline on Clinical Investigation of Medicinal Products for the Treatment of Multiple Sclerosis (CPMP/EWP/561/98 Rev. 1, November 2006).
19. EPAR, Rebif®, Scientific Discussion.
20. Fischer et al. (1999) "The Multiple Sclerosis Functional Composite measure (MSFC): an integrated approach to MS clinical outcome assessment" *Multiple Sclerosis.* 5(4):244-250.
21. Fisk et al. (1994) "Measuring the Functional Impact of Fatigue: Initial Validation of Fatigue Impact Scale", *Clin Inf Dis.* 18 Suppl 1:S79-83.
22. Fisk et al. (1994) "The Impact of Fatigue on Patients with Multiple Sclerosis", *Can J Neurol Sci.* 21:9-14.
23. Frohman et al. (2003) "The utility of MRI in suspected MS: report of the Therapeutics and Technology Assessment Subcommittee of the American Academy of Neurology", *Neurology.* Sep. 9, 2003, 61(5):602-11.
24. Giovannoni et al. (2010) "A placebo-controlled trial of oral cladribine for relapsing multiple sclerosis", *N Eng J Med.* 362:416-426.
25. Golder W. (2007) "Magnetic resonance spectroscopy in clinical oncology", *Onkologie.* 27(3): 304-9.
26. Grossman et al. (1994) Magnetization transfer: theory and clinical applications in neuroradiology", *RadioGraphics.* 14:279-290.
27. Guyatt et al. (1985) "The 6-minute walk: a new measure of exercise capacity in patients with chronic heart failure" Can Med Assoc J., 132:919-823.
28. Hartung et al. (2005) "Significance of neutralizing antibodies to interferon beta during treatment of multiple sclerosis: expert opinions based on the Proceedings of an International Consensus Conference", *Eur J Neurol.* 12:588-601.
29. Hauser et al. (1983) "Intensive immunosuppression in progressive multiple sclerosis", *New Engl J Med.* 308: 173-180.
30. Hohlfeld et al. (2000) "The neuroprotective effect of inflammation: implications for the therapy of multiple sclerosis", *J Neuroimmunol.* 107:161-166.
31. Jacobs et al. (1996) "Intramuscular interferon beta-1a for disease progression in relapsing multiple sclerosis", *Ann Neurol.* 39:285-294.
32. Kappos et al. (2010) "A placebo-controlled trial of oral fingolimod in relapsing multiple sclerosis", *N Eng J Med.* 362:387-401.
33. Kurtzke J F. (1983) "Rating neurologic impairment in multiple sclerosis: an expanded disability status scale (EDSS)", *Neurology* 33(11):1444-1452.
34. Learmonth Y C et al. (2013) BMC Neurology; 13:37.
35. Lublin and Reingold (1996) "Defining the clinical course of multiple sclerosis", *Neurol.* 46:907-911.
36. Lublin et al. (2014) "Defining the clinical course of multiple sclerosis" *Neurology.* 83:1-9
37. McDonald, (2001) "Guidelines from the International Panel on the Diagnosis of Multiple Sclerosis" *Ann. Neurol.* 50:121-127.
38. Mehta et al. (1996) "Magnetization transfer magnetic resonance imaging: a clinical review", *Topics in Magnetic Resonance Imaging* 8(4):214-30.

39. Miki et al. (1999) "Relapsing-Remitting Multiple Sclerosis: Longitudinal Analysis of MR Images—Lack of Correlation between Changes in T2 Lesion Volume and Clinical Findings", *Radiology.* 213:395-399.
40. Miller et al. (2007) "MRI outcomes in a placebo-controlled trial of natalizumab in relapsing MS", *Neurology.* 68:1390-1401.
41. Neuhaus et al. (2003) "Immunomodulation in multiple sclerosis: from immunosuppression to neuroprotection", *Trends Pharmacol Sci.* 24:131-138.
42. Noseworthy et al. (2000) "Multiple sclerosis", *N Engl J Med.* 343:938-952.
43. Noseworthy et al. (2000) "Linomide in relapsing and secondary progressive MS. Part 1: Trial Design and clinical results", *Neurology.* 54:1726-1733.
44. Panitch H, Goodin D S, Francis G, Chang P, Coyle P K, O'Connor P, Monaghan E, Li D, Weinsjenker B, for the EVIDENCE (Evidence of Interferon Dose-response: European North American Comparative Efficacy) Study Group and the University of British Columbia MS/MRI Research Group. (2002) "Randomized comparative study of interferon β-1a treatment regiments in MS", The EVIDENCE Trial. Neurology. 59:1496-1506.
45. PCT International Application Publication No. WO 2007/047863, published Apr. 26, 2007, international filing date Oct. 18, 2006.
46. PCT International Application Publication No. WO 2007/146248, published Dec. 21, 2007, international filing date Jun. 12, 2007.
47. Polman et al. (2005) "Diagnostic criteria for multiple sclerosis: 2005 revisions to the McDonald Criteria", Annals of Neurology, Volume 58 Issue 6, Pages 840-846.
48. Polman et al. (2005) "Treatment with laquinimod reduces development of active MRI lesions in relapsing MS", Neurology. 64:987-991.
49. Polman et al. (2006) "A randomized, placebo-controlled trial of natalizumab for relapsing multiple sclerosis", *N Eng J Med.* 354:899-910.
50. Poser et al. (1983) "New Diagnostic Criteria for Multiple Sclerosis: Guidelines for Research Protocols", *Annals of Neurology*, March 1983, 13(3):227-230.
51. Preiningerova J. (2009) "Oral laquinimod therapy in relapsing multiple sclerosis", *Expert Opin Investig Drugs.* 18:985-989.
52. PRISMS Study Group. Randomized double-blind placebo-controlled study of interferon β-1a in relapsing/remitting multiple sclerosis. *Lancet* 1998; 352:1498-1506.
53. Rosen Y. (2007) "The Recent advances in magnetic resonance neurospectroscopy", *Neurotherapeutics.* 27(3): 330-45.
54. Rudick et al. (1999) "Use of the brain parenchymal fraction to measure whole brain atrophy in relapsing-remitting MS: Multiple Sclerosis Collaborative Research Group". *Neurology.* 53:1698-1704.
55. Rudick, R. (1999) "Disease-Modifying Drugs for Relapsing-Remitting Multiple Sclerosis and Future Directions for Multiple Sclerosis Therapeutics", *Neurotherpatueics.* 56:1079-1084.
56. Runström et al. (2002) "Laquinimod (ABR-215062) a candidate drug for treatment of Multiple Sclerosis inhibits the development of experimental autoimmune encephalomyelitis in IFN-β knock-out mice", (Abstract), Medicon Valley Academy, Malmoe, Sweden.
57. Sandberg-Wollheim et al. (2005) "48-week open safety study with high-dose oral laquinimod in patients", *Mult Scler.* 11:S154 (Abstract).
58. SIENA and SIENAX available from the FMRIB Software Library, Oxford University. Oxford, UK; http://www.fmrib.ox.ac.uk/analysis/research/siena/siena.
59. Sorenson P S. (2006) "Neutralising antibodies to interferon-β—measurement, clinical relevance, and management", *J Neurol.* 253[Suppl 6]:VI/16-VI/22.
60. Sormani et al. (2004) "Measurement error of two different techniques for brain atrophy assessment in multiple sclerosis", Neurology. 62:1432-1434.
61. Sormani M P et al. (2013) Mult Scler; 19(Suppl 11): P1080.
62. Temple R. (2006) "Hy's law: predicting serious hepatoxicity", *Pharmacoepidemiol Drug Saf.* 15(4):241-3.
63. The IFNB Multiple Sclerosis Study Group. (1993) Interferon beta-1b is effective in relapsing-remitting multiple sclerosis. I. Clinical results of a multicenter, randomized, double-bind, placebo-controlled trial. *Neurology;* 43:655-661.
64. The IFNB Multiple Sclerosis Study Group. (1993) Interferon beta-1b is effective in relapsing-remitting multiple sclerosis. II. MRI analysis results of a multicenter, randomized, double-blind, placebo-controlled trial. *Neurology;* 43:662-667.
65. The National MS Society (USA), *The Disease Modifying Drug Brochure*, Oct. 19, 2006.
66. Thöne and Gold (2011) "Laquinimod: a promising oral medication for the treatment of relapsing-remitting multiple sclerosis", *Expert Opin Drug Metab Toxicol.* 2011 March; 7(3): 365-70.
67. US Food and Drug Administration, Center for Drug Evaluation and Research. Peripheral and Central Nervous System (PCNS) Advisory Committee. US Department of Health and Human Services 2006. Briefing Document. Biogen Idec Biologics Marketing Application STN 125104/15. Natalizumab (Tysabri) for Multiple Sclerosis. Dated Feb. 9, 2006. Pages 45-48.
68. Vollmer T et al. (2012) Neurology; 78(Suppl 1):S01.007.
69. Vollmer T et al. (2014) Presented at ECTRIMS/ACTRIMS; Sep. 10-13, 2014, Boston, Mass. Poster P062.
70. Vollmer T J et al. (2014) J Neurol; 261:773-783.
71. Yang et al., (2004) "Laquinimod (ABR-215062) suppresses the development of experimental autoimmune encephalomyelitis, modulates the Th1/Th2 balance and induces the Th3 cytokine TGF-β in Lewis rats", *J. Neuroimmunol.* 156:3-9.
72. Zou et al. (2002) "Suppression of experimental autoimmune neuritis by ABR-215062 is associated with altered Th1/Th2 balance and inhibited migration of inflammatory cells into the peripheral nerve tissue", *Neuropharmacology.* 42:731.

What is claimed is:

1. A method of reducing deterioration of ambulation of a human patient diagnosed to be afflicted with relapsing-remitting multiple sclerosis (RRMS) and to have a baseline disability score according to the Kurtzke Expanded Disability Status Scale (EDSS) of greater than 3, comprising periodically administering to only the patient diagnosed with RRMS and having a baseline EDSS score of greater than 3 an amount of laquinimod effective to reduce deterioration of the patient's ambulation.

2. The method of claim 1, wherein the amount of laquinimod is effective to reduce the patient's relapse rate.

3. The method of claim 1, wherein the amount of laquinimod is effective to reduce the patient's accumulation of physical disability.

4. The method of claim 1, wherein ambulation is assessed by the patient's Timed-25 foot walk test score.

5. The method of claim 1, wherein laquinimod is administered orally and/or daily.

6. The method of claim 1, wherein laquinimod is administered at a daily dose of 0.3 mg laquinimod.

7. The method of claim 1, wherein laquinimod is administered at a daily dose of 0.6 mg laquinimod.

8. The method of claim 1, wherein laquinimod is administered as adjunct therapy with another RRMS treatment.

9. The method of claim 8, wherein the other RRMS treatment is administration of interferon beta 1-a, interferon beta 1-b, glatiramer acetate, mitoxantrone or natalizumab.

10. A method of reducing deterioration of ambulation of a human patient diagnosed to be afflicted with RRMS, worsening MS and to have a baseline disability score according to the Kurtzke Expanded Disability Status Scale (EDSS) of greater than 3.0, comprising periodically administering to only the patient diagnosed with RRMS, worsening MS and having an EDSS score of greater than 3.0 an amount of laquinimod effective to reduce deterioration of the patient's ambulation.

11. The method of claim 10, wherein laquinimod is administered orally and/or daily.

12. The method of claim 10, wherein laquinimod is administered at a daily dose of 0.3 mg laquinimod.

13. The method of claim 10, wherein laquinimod is administered at a daily dose of 0.6 mg laquinimod.

14. The method of claim 10, wherein laquinimod is administered as adjunct therapy with another RRMS treatment.

15. The method of claim 14, wherein the other RRMS treatment is administration of interferon beta 1-a, interferon beta 1-b, glatiramer acetate, mitoxantrone or natalizumab.

16. The method of claim 1, wherein the patient has mobility impairment.

17. The method of claim 1, wherein the patient has a baseline EDSS score of 3.5-5.5.

18. The method of claim 1, wherein the laquinimod is laquinimod sodium.

19. The method of claim 16, wherein the mobility impairment is an ambulatory impairment.

20. The method of claim 19, wherein the patient is not ambulatory.

21. The method of claim 10, wherein the amount of laquinimod is effective to reduce the patient's relapse rate.

22. The method of claim 10, wherein the amount of laquinimod is effective to reduce the patient's accumulation of physical disability.

23. The method of claim 10, wherein ambulation is assessed by the patient's Timed-25 foot walk test score.

24. The method of claim 10, wherein the patient has a baseline EDSS score of 3.5-5.5.

25. The method of claim 10, wherein the laquinimod is laquinimod sodium.

26. The method of claim 10, wherein the patient has mobility impairment.

27. The method of claim 26, wherein the mobility impairment is an ambulatory impairment.

28. The method of claim 27, wherein the patient is not ambulatory.

* * * * *